United States Patent
Varadi et al.

(10) Patent No.: US 10,900,979 B2
(45) Date of Patent: Jan. 26, 2021

(54) METHODS FOR TESTING EFFECTIVENESS OF A VON WILLEBRAND FACTOR USED IN TREATING VON WILLEBRAND DISEASE (VWD)

(71) Applicants: Baxalta GmbH, Glattpark (CH); Baxalta Incorporated, Bannockburn, IL (US)

(72) Inventors: Katalin Varadi, Vienna (AT); Hanspeter Rottensteiner, Vienna (AT); Peter Turecek, Klosterneuburg (AT); Hans-Peter Schwarz, Vienna (AT); Jutta Schreiner, Vienna (AT)

(73) Assignees: Baxalta Incorporated, Bannockburn, IL (US); Baxalta GmbH, Glattpark (CH)

(*) Notice: Subject to any disclaimer, the term of this patent is extended or adjusted under 35 U.S.C. 154(b) by 0 days.

(21) Appl. No.: 16/248,868

(22) Filed: Jan. 16, 2019

(65) Prior Publication Data

US 2019/0145989 A1 May 16, 2019

Related U.S. Application Data

(60) Division of application No. 15/345,070, filed on Nov. 7, 2016, now Pat. No. 10,209,263, which is a continuation of application No. 14/549,404, filed on Nov. 20, 2014, now Pat. No. 9,488,651, which is a division of application No. 14/078,324, filed on Nov. 12, 2013, now Pat. No. 9,110,085, which is a division of application No. 13/795,214, filed on Mar. 12, 2013, now Pat. No. 8,623,612, which is a division of application No. 12/630,509, filed on Dec. 3, 2009, now Pat. No. 8,415,114.

(60) Provisional application No. 61/120,202, filed on Dec. 5, 2008.

(51) Int. Cl.
| C12Q 1/56 | (2006.01) |
| G01N 33/86 | (2006.01) |
| C12Q 1/37 | (2006.01) |
| G01N 33/573 | (2006.01) |

(52) U.S. Cl.
CPC ............. *G01N 33/86* (2013.01); *C12Q 1/37* (2013.01); *C12Q 1/56* (2013.01); *G01N 33/573* (2013.01); *G01N 2333/755* (2013.01); *G01N 2333/96486* (2013.01); *G01N 2800/224* (2013.01); *G01N 2800/52* (2013.01)

(58) Field of Classification Search
None
See application file for complete search history.

(56) References Cited

U.S. PATENT DOCUMENTS

| 7,291,479 | B2 | 11/2007 | Boehm | |
| 7,575,872 | B2 | 8/2009 | Soejima et al. | |
| 7,718,763 | B2 | 5/2010 | Miyata et al. | |
| 8,067,221 | B2 | 11/2011 | Soejima et al. | |
| 8,415,114 | B2 * | 4/2013 | Varadi | C12Q 1/37 435/13 |
| 8,623,612 | B2 * | 1/2014 | Varadi | C12Q 1/37 435/13 |
| 8,852,888 | B2 | 10/2014 | Grillberger et al. | |
| 9,110,085 | B2 * | 8/2015 | Varadi | C12Q 1/37 |
| 9,488,651 | B2 * | 11/2016 | Varadi | C12Q 1/37 |
| 10,209,263 | B2 * | 2/2019 | Varadi | C12Q 1/37 |
| 10,758,599 | B2 * | 9/2020 | Matthiessen | A61K 9/19 |
| 2005/0239153 | A1 | 10/2005 | Boehm | |
| 2007/0015703 | A1 | 1/2007 | Wagner et al. | |
| 2007/0065895 | A1 | 3/2007 | Miyata et al. | |
| 2010/0115637 | A1 | 5/2010 | Schwarz et al. | |
| 2010/0144634 | A1 | 6/2010 | Zheng et al. | |
| 2011/0229455 | A1 | 9/2011 | Matthiessen et al. | |
| 2012/0034674 | A1 | 2/2012 | Grillberger et al. | |
| 2012/0035110 | A1 | 2/2012 | Grillberger et al. | |
| 2012/0142036 | A1 | 6/2012 | Chen et al. | |

FOREIGN PATENT DOCUMENTS

| EP | 1988174 A1 | 11/2008 |
| EP | 1852442 B1 | 3/2012 |
| JP | 2007024839 A | 2/2007 |
| JP | 2007248395 A | 9/2007 |

(Continued)

OTHER PUBLICATIONS

Mannucci P. et al. Pharmacokinetics and Safety of a Novel Recombinant Human von Willbrand Factor . . . Blood 122(5)648-657, 2013. Legible copy provided. (Year: 2013).*
Aronsori et al., ADAMTSI3 proteolysis of von Willebrand factor: What is bite sized (abstract), Blood 1 02:544A-45A (2003).
Extended European Search Report dated Jul. 5, 2018 issued for European Patent Application No. 18173838.6.
Fuchigami et al., Changes in plasma Von Willebrand factor-cleaving protease (ADAMTS13) levels in patients with unstable angina, Thrombosis Research 122:618-23 (2008).
Furlan et al., von Willebrand factor-cleaving protease in thrombotic thrombocytopenic purpura and the hemolytic-uremic syndrome. N. Engl. J. Med. 339(22): 1578-84 (1998).

(Continued)

*Primary Examiner* — Ralph J Gitomer
(74) *Attorney, Agent, or Firm* — Troutman Pepper Hamilton Sanders LLP

(57) ABSTRACT

The invention generally relates to methods of testing the effectiveness of a von Willebrand factor (VWF) in treating von Willebrand disease (VWD) in a subject comprising measuring VWF cleavage fragments in a blood sample from the subject before and after treatment. In particular, the invention relates to methods of measuring VWF cleavage fragments, wherein an increase in VWF cleavage fragments after the treatment indicates that endogenous a disintegrin and metalloproteinase with a thrombospondin type 1 motif, member 13 (ADAMTS13) in the subject is cleaving the VWF and wherein a decrease or absence of VWF cleavage fragments after the treatment indicates that endogenous ADAMTS13 in the subject is not cleaving the VWF.

23 Claims, 21 Drawing Sheets

(56) References Cited

FOREIGN PATENT DOCUMENTS

| WO | 2003016492 A2 | 2/2003 |
|---|---|---|
| WO | 2005008241 A | 1/2005 |
| WO | 2006019431 A2 | 2/2006 |

OTHER PUBLICATIONS

Furlan et al., Assays of von Willebrand Factor Cleaving Protease. Seminars in Thrombosis and Hemostasis, 25(2):167-172 (2002).
Gerritsen et al., Assay of von Willebrand factor (vWF)-cleaving protease based on decreased collagen binding affinity of degraded vWF, Thromb. Haemost. 82: 1386-9 (1999).
Haberichter et al., Assay of the von Willebrand factor (VWF) propeptide to identify patients with type 1 von Willebrand disease with decreased VWF survival, Blood 108:3344-51 (2006).
International Search Report of the International Searching Authority, European Patent Office, PCT/US2009/066588, dated Mar. 30, 2010.
Japanese Journal of Transfusion Medicine. 47(3): 497-99 (2001). [English translation to follow].
Kato et al., Novel monoclonal antibody-based enzyme immunoassay for determining plasma levels of ADAMTS13 activity, Transfusion 46:1444-52 (2006).
Maekawa et al., Thrombotic thrombocytopenic purpura associated with ticlopidine following coronary stenting-Measurement of von Willeband factor-cleaving protease. Heart 36(2): 103-6 (2004). [English translation to follow].
Moake, Studies on the pathophysiology of thrombotic thrombocytopenic purpura, Semin. Hematol. 34:83-9 (1997).
Moake, von Willebrand factor, ADAMTS-13, and thrombotic thrombocytopenic purpura, Semin. Hematol. 41 :4-14 (2004).
Plaimauer et al., Cloning, expression, and functional characterization of the von Willebrand factorcleavinQ protease (ADAMTSI3), Blood 100:3626-32 (2002).
Pressman et al., Development and performance of the GTI ADAMTS-13 activity assay. Blood 106(11, part 2):105B (2005).
Reiter et al., Changes in ADAMTSI3 (von-Willebrand-factor-cleaving protease) activity after induced release of von Willebrand factor during acute systemic inflammation. Thromb. Haemost. 93(3): 554-8 (2005).
Reiter et al., Changes in von Willebrand factor-cleaving protease (ADAMTSI3) activity after infusion of desmopressin, Blood 101 :946-8 (2003).
Rieger et al., Relation between ADAMTS13 activity and ADAMTS13 antigen levels in healthy donors and patients with thrombotic microangiopathies (TMA), Thromb. Haemost. 95:212-20 (2006).
Schneppenheim et al., von Willebrand factor cleavage protease and ADAMTS13 mutations in childhold TTP. Hemost. Thromb. Vasco Biol. 101 (5): 1845-50 (2003).
Shenkman et al., ADAMTS-13 regulates platelet adhesion under flow. A new method for differentiation between inherited and acquired thrombotic thrombcytopenic purpura. Thromb. Haemost. 96(2): 160-6 (2006).

Shim et al., Platelet-VWF complexes are preferred substrates of ADAMTS13 under fluid shear stress, Blood 111 :651-7 (2008).
Studt et al., Measurement of von Willebrand Factor Cleaving Protease Activity in Plasma, J of Thrombosis and Haemostasis 1(9) 1882-1887 (2003).
Tan et al., What a polyclonal antibody sees in von Willebrand factor, Thromb. Res. 121 :519-26 (2008).
Tripoidi et al., Measurement of von Willebrand Factor Cleaving Protease . . . J of Thrombosis and Haemostasis 2(9) 1601-1609 (2004).
Tsai et al., Physiologic cleavage of von Willebrand Factor by a plasma protease is dependent on its conformation and requires calcium ion. Blood, 87(10): 4235-44 (1996).
Tsai et al., Shear stress enhances the proteolysis of von Willebrand factor in normal plasma. Blood 83(8): 2171-9 (1994).
Turecek et al., Biochemical and functional characterization of a serum-free rVWF drug candidate, Blood 108:Abstract 1017 (2006).
Turecek et al., Comparative study on collagen-binding enzyme-linked immunosorbent assay and ristocetin cofactor activity assays for detection of functional activity of con Willebrand factor, Semin. Thromb. Hemost. 28:149-60 (2002).
Turecek et al., In vivo characterization of recombinant von Willebrand factor in dogs with von Willebrand disease, Blood 90:3555-67 (1997).
Varadi et al., Thrombin Mediated in Vitro Processing of Pro von Willebrand Factor, Thromb. Haemost. 86(6):1449-58 (2001).
Veyradier et al., Assays of ADAMTS-13 activity. Semin. Hematol. 41 (1): 41-7 (2004).
VWF to Setsudan Koso ADAMTS13 no Kensa [6. Investigation of VWF and cleavage enzyme ADAMTS13] Medical Technology, 35(2): 161-7 (2007). [English translation to follow].
Zhao et al., VWF-cleaving protease ADAMTS13 reduces brain injury following ischemic stroke in mice: Essential role for VWF in stroke, Blood 112: Abstract 259 (2008).
Hisahide Hiura, "Development of the new measuring method of ADAMTS13 activity important for diagnosis of TMA, and the index of a platelet transfusion", Clinical Pathology, Jan. 2007, vol. 55, No. 1, pp. 69-75.
Fisher, B.E. et al., "Structural analysis of recombinant von Willebrand factor produced at industrial scale fermentation of transformed CHO cells co-expressing recombinant furin", FEBS LETT., Nov. 20, 1995, vol. 375, No. 3, pp. 259-262.
Mannucci et al., "Pharmacokinetics and safety of a novel recombinant human von Willebrand factor manufactured with a plasma-free method: a prospective clinical trial", Blood, 2013, vol. 122 (5), pp. 648-657.
Schlokat, U. et al., "Production of highly homogeneous and structurally intact recombinant von Willebrand factor multimers byfurin-mediated propeptide removal in vitro", Biotechnol. Appl. Biochem., Dec. 1996, vol. 24, No. 3, pp. 257-267.
Siekmann, J. et al., "The determination of von Willebrand factor activity by collagen binding assay", Haemophilia (1998), vol. 4 (Suppl. 3), pp. 15-24.

* cited by examiner

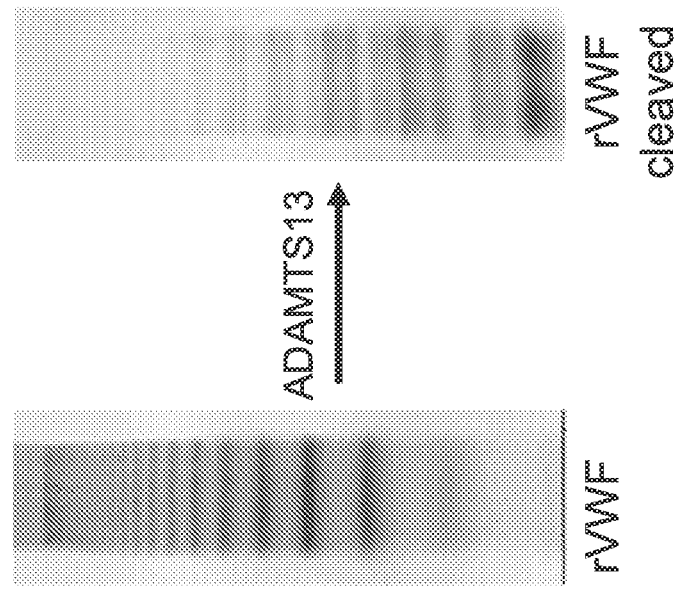
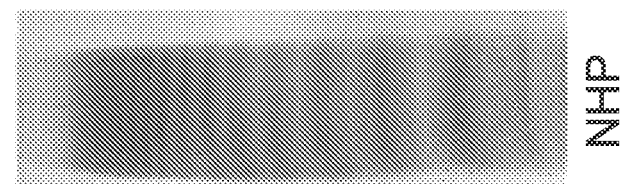

| | Cynomolgus monkey | Rhesus monkey | Rabbit New Zealand White | Pig Yorkshire | Dog Beagle | Guinea pig Dunkin Hartley | Rat Sprague Dawley | Mouse VWF deficient (C57BL) | Mouse ADAMTS13 deficient (C57BL) |
|---|---|---|---|---|---|---|---|---|---|
| FRETS-VWF73 (%) | 97 | 116 | 93 | 52 | 190 | Below detection limit | Below detection limit | Below detection limit | Below detection limit |
| CBA (%) | 51 | 55 | 98 | 36 | 40 | Below detection limit | Below detection limit | Below detection limit | Below detection limit |

*FIG. 4*

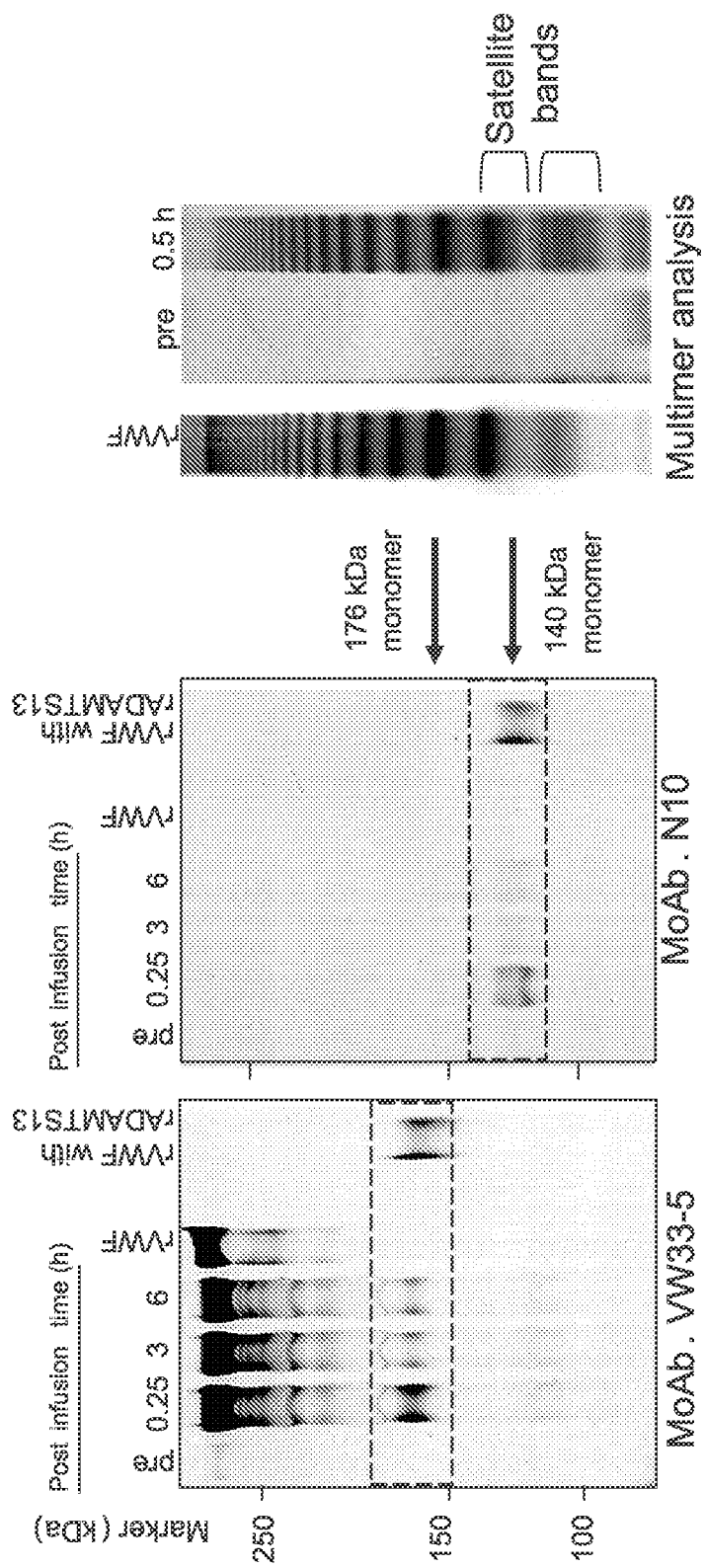

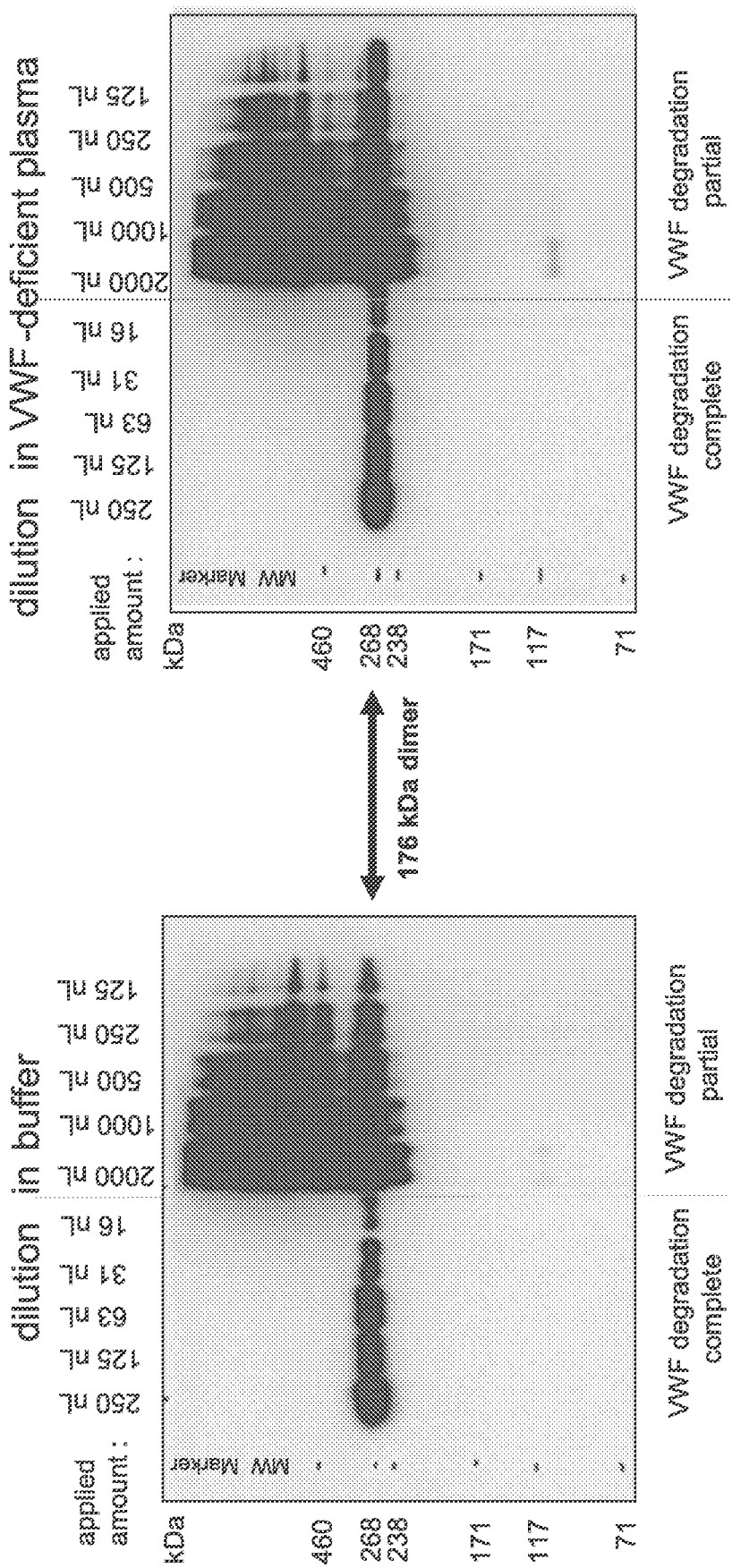

METHODS FOR TESTING EFFECTIVENESS OF A VON WILLEBRAND FACTOR USED IN TREATING VON WILLEBRAND DISEASE (VWD)

RELATED APPLICATIONS

This application is a divisional of U.S. patent application Ser. No. 15/345,070, filed Nov. 7, 2016, which is a continuation of U.S. patent application Ser. No. 14/549,404, filed on Nov. 20, 2014, now U.S. Pat. No. 9,488,651, which is a divisional of U.S. patent application Ser. No. 14/078,324, filed on Nov. 12, 2013, now U.S. Pat. No. 9,110,08, which is a divisional of U.S. patent application Ser. No. 13/795,214, filed on Mar. 12, 2013, now U.S. Pat. No. 8,623,612, which is a divisional of U.S. patent application Ser. No. 12/630,509, filed on Dec. 3, 2009, now U.S. Pat. No. 8,415,114, which claims benefit of U.S. Provisional Application No. 61/120,202, filed on Dec. 5, 2008, each of which is hereby incorporated herein in its entirety by reference thereto.

FIELD OF THE INVENTION

The invention generally relates to methods of measuring cleaved von Willebrand factor (VWF) fragments. More specifically, the invention relates to methods of measuring the ability of a disintegrin and metalloproteinase with a thrombospondin type 1 motif, member 13 (ADAMTS13) to cleave VWF in vivo. The invention also relates to the use of various animal models which demonstrate ADAMTS13 activity similar to that of a human.

BACKGROUND OF THE INVENTION

Circulating von Willebrand factor (VWF) in healthy humans is composed of a series of high molecular weight multimers ranging from about 450,000 to about 20 million Dalton (Da) or even higher molecular weight upon release from storage pools. VWF mediates primary hemostasis supporting the adhesion of platelets to damaged blood vessels. In addition to being necessary for platelet aggregation, VWF is required for the stabilization of circulating Factor VIII (FVIII). In von Willebrand disease (VWD), at least one of these functions of VWF is reduced, resulting in clinical symptoms of varying severity.

The degree of VWF multimerization plays an important role in primary hemostatic function and correlates with the ability to promote platelet aggregation. The lack of high multimer forms of VWF results in decreased platelet aggregation, as seen in subjects with Type II VWD. On the other hand, the accumulation of ultra-large VWF multimers can cause thrombosis in the microvasculature. In healthy individuals the multimeric size of VWF is regulated by the presence of ADAMTS13. Due to ADAMTS13 cleavage of the VWF monomers between $Tyr^{1605}$ and $Met^{1606}$, the multimer pattern of VWF shows a characteristic "triplet" structure. Individuals lacking ADAMTS13 have an increased portion of ultra-large VWF multimers with a reduced triplet structure. These individuals often develop a syndrome called thrombotic thrombocytopenic purpura (TTP) that is characterized by the formation of thrombi in the microvasculature with platelet consumption.

ADAMTS13 can only cleave VWF when its conformation changes from a globular to an extended form, a change which normally occurs only under shear stress. ADAMTS13 activity is usually measured in vitro under denaturing conditions to induce the conformational change, or by using a peptide substrate.

Currently, no method is available to test the in vivo activity of ADAMTS13 in the presence of endogenous VWF. Thus, there exists a need in the art to develop new methods of measuring the cleavage of VWF by ADAMTS13. There also remains a need in the art to determine the efficacy of new recombinant VWF and ADAMTS13 products during preclinical and clinical studies. In addition, there is a need in the art for new methods to test the effectiveness of new therapies in the treatment of ADAMTS13 deficiencies in vivo.

SUMMARY OF THE INVENTION

The invention addresses one or more needs in the art relating to methods of measuring the in vivo activity of ADAMTS13 and methods of evaluating new types of recombinant von Willebrand Factor (VWF) and recombinant ADAMTS13 in vivo for their subsequent administration to a subject in need thereof In one aspect, the invention includes methods of detecting VWF fragments in the blood of a subject. Such methods show the in vivo activity of ADAMTS13 by detection (i.e., visualization and even quantification) of the amount of circulating fragments of cleaved VWF. In one aspect, the methods are based on SDS-PAGE combined with immunoblotting using specific antibodies against VWF. In some aspects, the VWF antibodies are specific for different fragments of VWF. Such antibodies are polyclonal or monoclonal. In further aspects, a blood sample of a subject is applied to a gel, the gel is subjected to immunoblotting with a VWF antibody conjugated to a marker, and the marker is detected with enhanced chemiluminescence.

In another aspect, the invention includes methods for determining aberrant ADAMTS13 activity in vivo comprising the step of measuring VWF cleavage fragments in a blood sample from a test subject, wherein a change in VWF cleavage fragment levels in the blood sample of the test subject compared to VWF cleavage fragment levels in a blood sample from a control subject known to have normal ADAMTS13 activity indicates aberrant in vivo ADAMTS13 activity in the test subject.

The invention also includes methods for measuring ADAMTS13 activity in a blood sample from a subject comprising the steps of: measuring VWF cleavage fragments in the blood sample; comparing the VWF cleavage fragments to a reference curve of completely degraded VWF; and quantifying the VWF cleavage fragments based on the reference curve, wherein an amount of VWF cleavage fragments correlates with an amount of ADAMTS13 activity.

In another aspect, the invention includes methods for testing effectiveness of a treatment for increasing ADAMTS13 activity or concentration in a subject comprising measuring VWF cleavage fragments in a blood sample from the subject before and after the treatment, wherein an increase in VWF cleavage fragments after the treatment indicates that the treatment is effective in increasing ADAMTS13 activity or concentration in the subject.

In an additional aspect, the invention includes methods for testing effectiveness of a treatment for von Willebrand disease (VWD) associated with a deficiency or dysfunction of ADAMTS13 in a subject comprising measuring VWF cleavage fragments in a blood sample from the subject before and after treatment, wherein an increase in VWF cleavage fragments after the treatment indicates that the treatment is effective in treating the disease.

In a further aspect, the invention includes methods for testing effectiveness of a VWF used in treating VWD in a subject comprising measuring VWF cleavage fragments in a blood sample from the subject before and after treatment, wherein an increase in VWF cleavage fragments after the treatment indicates that endogenous ADAMTS13 in the subject is cleaving the VWF and wherein a decrease or absence of VWF cleavage fragments after the treatment indicates that endogenous ADAMTS13 in the subject is not cleaving the VWF.

In various aspects, the methods of the invention allow the comparison of species-species interaction of various sources of VWF and ADAMTS13 from the different species or animal models.

In various aspects, the types of treatment included in the methods of the invention include the administration of ADAMTS13 to the subject.

The invention further includes methods for testing the effectiveness of a treatment for thrombotic thrombocytopenic purpura (TTP) in a subject comprising measuring VWF cleavage fragments in a blood sample from the subject before and after the treatment, wherein a decrease in the amount of ultra-large multimers of VWF with a reduced triplet structure after the treatment indicates that the treatment is effective in increasing ADAMTS13 activity or concentration in the subject.

In various aspects of the invention, measuring of VWF cleavage fragments or VWF level comprises performing Western blot analysis with a VWF antibody to visualize VWF cleavage fragments. In one aspect, Western blot analysis is carried out under non-reducing conditions to increase sensitivity. In other aspects, reducing conditions are also used. In further aspects of the methods of the invention, VWF fragments are visualized through use of a VWF antibody conjugated to a marker. In various aspects, the marker is alkaline phosphatase (ALP) or horseradish peroxidase (HRP). In even further aspects, the marker is detected with enhanced chemiluminescence (ECL).

In some aspects of the invention, VWF multimers are visualized by using high resolution horizontal SDS-agarose gel electrophoresis followed by immunostaining with a polyclonal rabbit anti-human VWF antibody. In various other aspects of the invention, the VWF antibody is monoclonal or polyclonal. Other types of antibodies known in the art are also contemplated for use in the methods of the invention. In even further aspects, VWF cleavage fragment level is detected at a sensitivity level of about 0.025 to about 0.05 Ag U/mL VWF.

In other aspects, the invention includes methods of assessing ADAMTS13 activity in a subject comprising comparing total VWF and VWF cleavage fragment level in a blood sample of the subject to a reference curve of increasingly degraded or digested VWF, wherein the VWF cleavage fragment level in the blood sample correlates to an ADAMTS13 activity deduced from the reference curve.

In various aspects, the VWF cleavage fragment level in the blood sample of the test subject is increased compared to VWF cleavage fragment level in a blood sample from a control subject. In other aspects, the VWF cleavage fragment level in the blood sample of the test subject is decreased compared to VWF cleavage fragment level in a blood sample from a control subject.

In some aspects, a change in VWF cleavage fragment level is detected by measuring the level of one or more VWF fragments. In certain aspects, the VWF fragment that is measured is a 140 kDa VWF fragment or a 176 kDa VWF fragment. In particular aspects, the VWF fragment that is measured is a 176 kDa VWF fragment.

The invention includes methods for measuring ADAMTS13 activity in a subject comprising the steps of: adding VWF to a blood sample from the subject; measuring VWF cleavage fragments in the blood sample after exposure of the sample in the presence and absence of shear stress; comparing the VWF cleavage fragments to a reference curve of completely degraded VWF or to a reference curve from diluted human or animal plasma; and quantifying the VWF cleavage fragments based on the reference curve, wherein an amount of VWF cleavage fragments correlates with an amount of ADAMTS13 activity in the sample. In one aspect, the VWF is an intact recombinant VWF (rVWF) that is not yet cleaved by ADAMTS13. In some aspects, the shear stress comprises a shear rate of about 100 s-1 to about 10,000 s-1 at a temperature of about 20° C. to about 40 °C. for a period of time. In other aspects, the shear rate is about 1,000 s-1 to about 8,000 s-1. In one aspect, the shear rate is about 6,000 s-1. In various aspects, the temperature is about 30° C. to about 40° C. In one aspect, the temperature is about 37° C. In some aspects, the period of time ranges from about 30 seconds to about 1 hour. In other aspects, the time ranges from about 15 minutes to about 30 minutes. In one aspect, the time is about 30 minutes. In another aspect, the time is about 15 minutes.

In various aspects, the blood sample in the methods of the invention is plasma or serum. In particular aspects, the blood sample is plasma. In other aspects, the blood sample is serum. In other aspects, the blood sample is plasma that also contains cellular components such as platelets and white blood cells.

In further aspects, the subject in the methods of the invention is a mammal. In some aspects the mammalian subject is human, rabbit, monkey, dog, rat, mouse, or pig. In other aspects, the mammalian subject is human, rabbit, monkey, or dog. In a particular aspect, the subject is human.

BRIEF DESCRIPTION OF THE DRAWING

A further illustration of the invention is given with reference to the accompanying drawings, which are set out below in FIGS. 1-18.

FIGS. 1A-1B show the changes in multimeric structure of rVWF after cleavage by human ADAMTS13.

FIG. 4 shows ADAMTS13 activity, expressed as a percentage of normal human plasma (NHP), as measured by FRETS and VWF:CBA assays.

FIGS. 8A, 8B and 8C show specific in vivo cleavage of rVWF (1200 IU VWF:RCo/kg) by ADAMTS13 (140 kDa and 176 kDa fragments) in rabbits. VWF fragments were detected with monoclonal antibodies by immunoblotting with reducing SDS-PAGE (FIGS. 8A and B). As controls, uncleaved rVWF and rVWF cleaved with rADAMTS13 in vitro are shown. Characteristic changes in multimer pattern shortly after rVWF administration are also seen (FIG. 8C).

FIGS. 12A-12B show completely and partially ADAMTS13-degraded rVWF (1 Ag U/mL) measured in buffer and in VWF-deficient plasma with Western blotting under non-reducing conditions after 15 seconds of exposure with the polyclonal rabbit anti-human VWF antibody. Reducing conditions were not sensitive enough to visualize results. No differences between dilutions in buffer (FIG. 12A) and in VWF-deficient plasma (FIG. 12B) were detected.

DETAILED DESCRIPTION OF THE INVENTION

Figures 2A, 2B:
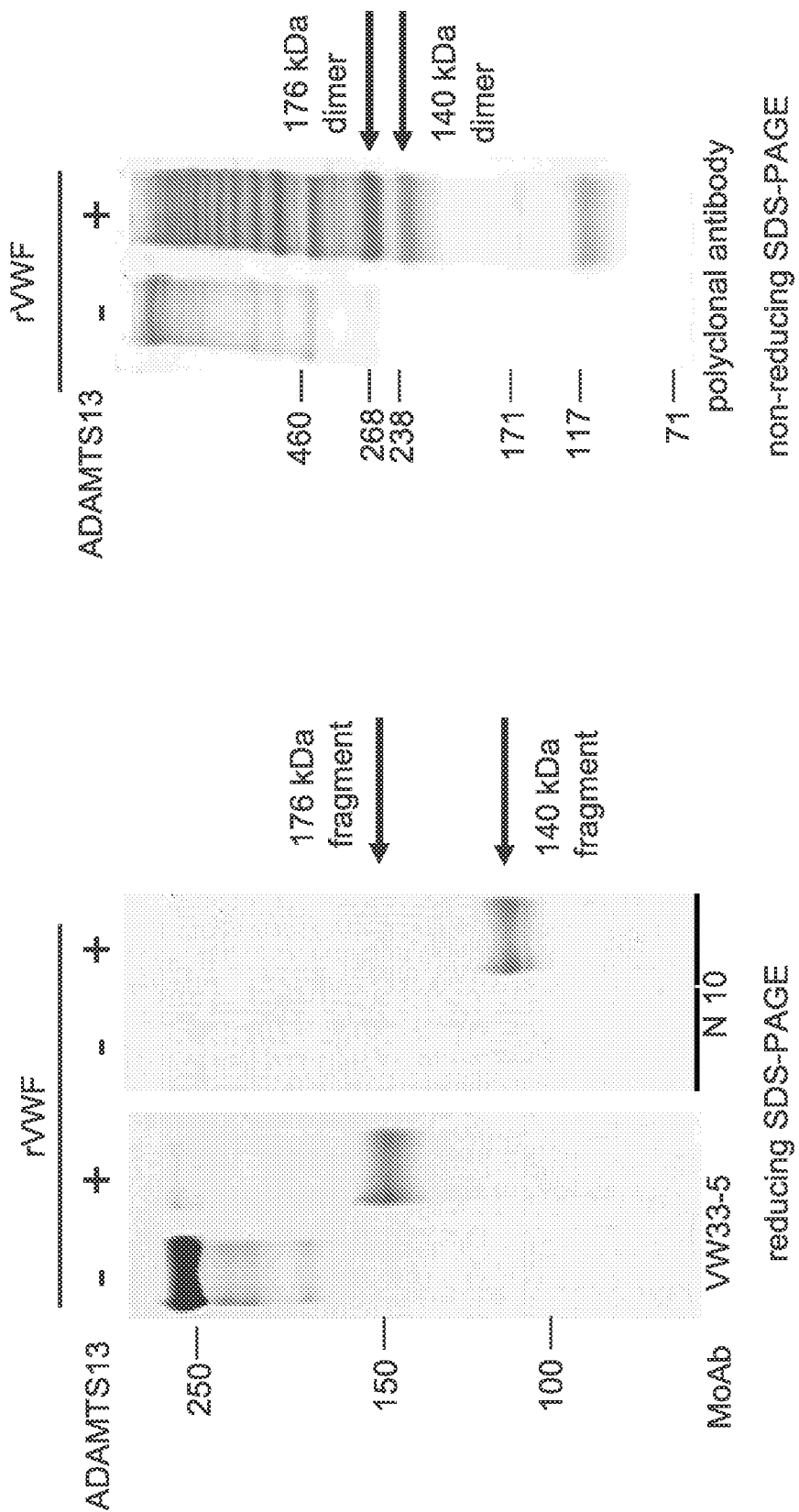
FIGS. 2A-2B show specific cleavage of rVWF monomers by ADAMTS13 as detected by immunoblotting with VWF antibodies.

The present invention provides methods of measuring ADAMTS13 activity by measuring the in vivo cleavage of VWF or rVWF by ADAMTS13. The invention also provides methods for determining if VWF is normally processed. The invention addresses a need in the art for improved methods to test effectiveness of new therapies in treatment of von Willebrand disease (VWD) and in treatment of thrombotic thrombocytopenic purpura (TTP) and other disorders associated with aberrant levels of ADAMTS13.

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

It is noted here that, as used in this specification and the appended claims, the singular forms "a," "an," and "the" include plural reference unless the context clearly dictates otherwise.

As used herein, the following terms have the meanings ascribed to them unless specified otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "aberrant" refers to abnormal, atypical, or unnatural level or activity of a polypeptide, protein or enzyme in a test subject compared to the level or activity of the polypeptide, protein or enzyme in a normal or control subject. Such abnormal level or activity may reflect a lower level, a lower activity, or a complete deficiency.

The term "VWF cleavage fragment" or "VWF fragments" or "VWF cleavage products" are used interchangeably herein and refer to fragments of VWF which result from protease cleavage. In one aspect, the protease cleaving VWF is ADAMTS13. ADAMTS13, also called VWF-cleaving protease (VWFCP), is a zinc-containing metalloprotease enzyme that cleaves VWF. ADAMTS13 is secreted in blood and degrades large VWF multimers, decreasing their activity. ADAMTS13 consists of multiple structural and functional domains, and these domains may participate in the recognition and binding of ADAMTS13 to VWF. The term "multimers" or "multimer forms" are used interchangeably herein. The ULVWF multimers are cleaved by ADAMTS13 as they are secreted from endothelial cells. Thus, the terms "ADAMTS13" and "VWFCP" are used interchangeably.

The term "visualized" or "detected" are used interchangeably herein when discussing the examination of VWF cleavage fragment level(s) on immunoblots or Western blots. Likewise, the term "level" or "levels" refers to the amount or concentration of VWF visualized, detected, or measured in a blot or assay.

The term "subject" or "test subject" or "subject in need thereof" may be used interchangeably herein and refers to any mammal. In various aspects, the subject is human, rabbit, monkey, or dog. Like humans, dogs are also known to suffer from VWD.

The term "blood" or "blood sample" may be used interchangeably herein. In various aspects, the blood is plasma or serum. Thus, the terms "blood", "blood sample", "plasma", "plasma sample", "serum" and "serum sample" are used interchangeably herein.

The term "endogenous" refers to a polypeptide or polynucleotide or other compound that is expressed naturally in a host organism, or originates within a cell, tissue or organ. "Exogenous" refers to a polypeptide, polynucleotide or other compound that originates from outside of a cell, tissue or organ outside of a host organism.

The term "polypeptide" refers to a polymer composed of amino acid residue linked via peptide bonds. Synthetic polypeptides are synthesized, for example, all or in part using an automated polypeptide synthesizer. The term "protein" typically refers to large polypeptides. The term "peptide" typically refers to short polypeptides.

The term "ADAMTS13" or "recombinant ADAMTS13" or "rADAMTS13" may be used interchangeably herein and refers to a disintegrin and metalloproteinase with a thrombospondin type 1 motif, member 13 polypeptide.

The term "VWF" or "recombinant VWF" or "rVWF" may be used interchangeably herein and refers to von Willebrand factor polypeptide.

The term "agent" or "compound" describes any molecule with the capability of affecting a biological parameter in the mammalian subject of the invention.

The methods of the invention included the use of various assays to measure ADAMTS13 activity. In some aspects, cleavage of rVWF by ADAMTS13 is carried out as described by Gerritsen et al. (*Thromb. Haemost.* 82: 1386-1389, 1999) with minor modifications. Recombinant VWF is digested with $Ba^{2+}$-activated ADAMTS13 under denaturing conditions. Plasma samples are diluted 1:20 in 5 mM Tris, 1.5 M urea, pH 8.0 (50 mU/mL ADAMTS13 activity), mixed with 9.3 mM $BaCl_2$ to activate ADAMTS13 and 1 IU/mL of human rVWF (final concentration) and incubated at 37° C. for 24 h. The reactions are stopped by adding $Na_2SO_4$ (8.25 mM). The solution is centrifuged and the resulting supernatant used for further analysis. As a positive control, 1 IU/mL of rVWF is incubated with human rADAMTS13 (50 mU/mL) under conditions that are otherwise identical to those used for the test item.

In other aspects of the invention, VWF antigen is determined in plasma samples. VWF:Ag was determined with an ELISA using commercially available polyclonal rabbit anti-VWF antibodies (Dako, Glostrup, Denmark) as described by Tan et al. (*Thromb. Res.* 121: 519-526, 2008).

In another aspect of the invention, ADAMTS13 activity is measured using a fluorescent-labeled synthetic VWF peptide composed of 73 amino acids (FRETS-VWF73, Peptides Institute, Osaka, Japan) according to manufacturer's instructions. Plasma samples are measured against a reference curve of diluted normal human plasma.

In even further aspects of the invention, determination of collagen-binding activity (VWF:CBA) is carried out. Binding of rVWF to collagen in some aspects is determined according to a published ELISA-based method (Turecek et al., *Semin. Thromb. Hemost.* 28: 149-160, 2002). In some aspects, the collagen source is human collagen type III from Southern Biotechnology Associates (Birmingham, Ala.). Bound rVWF is detected with polyclonal anti-VWF antibody conjugated with HRP (Dako).

In yet another aspect of the invention, VWF multimer analysis is carried out. In some aspects, the multimeric structure of rVWF is analyzed by high-density horizontal SDS agarose gel electrophoresis as described by Turecek et al. (*Blood* 90: 3555-3567, 1997). Samples are diluted to 1.0 IU/mL VWF:Ag, and incubated with Tris-EDTA-SDS buffer. The multimers contained in the solution are separated under non-reducing conditions on a 2.5% high-resolution agarose gel. VWF multimers are visualized in the gel by immunostaining with a polyclonal rabbit anti-human VWF antibody (Dako), followed by alkaline-phosphatase (ALP)-conjugated anti-rabbit IgG using the ALP color development kit from Bio-Rad (Richmond, Calif, USA).

The invention also includes the analysis of specific ADAMTS13 cleavage products. ADAMTS13-mediated cleavage in some aspects is detected by SDS-PAGE and Western blot analysis using either a polyclonal anti-human VWF antibody (Dako) or in some aspects one of the following mouse monoclonal antibodies: VW33-5, directed against the V8 protease fragment I of VWF (TaKaRa Bio Europe, Saint-Germain-en-Laye, France); VW92-3, directed against the V8 protease fragment III of VWF under non-reducing conditions (TaKaRa Bio Europe); EsvWF10, which recognizes the A1 domain of VWF under reducing conditions (American Diagnostica, Stamford, Calif.), and N10, which detects the epitope generated upon ADAMTS13 cleavage in the N-terminal fragment (Kato et al., Transfusion 46: 1444-1452, 2006). In some aspects, antibodies are used with ALP-conjugated goat anti-mouse secondary antibodies and the ALP detection kit (Bio-Rad). In other aspects, a horseradish peroxidase (HRP)-conjugated polyclonal anti-VWF antibody from rabbit (Dako) is used with the ECL detection system (GE Healthcare, Munich, Germany) to circumvent secondary antibodies reacting with endogenous immunoglobulins in mouse and rabbit plasma.

The invention also includes methods of carrying out in vivo cleavage of rVWF in different animal species. In some aspects, in vivo susceptibility of human rVWF to ADAMTS13 cleavage is determined by injecting rabbits and cynomolgus monkeys with rVWF at doses of 1200, 600, 300, and 100 VWF:RCo IU/kg body weight (BW) and VWF- or ADAMTS13-deficient mice with rVWF at a dose of 2000 VWF:RCo IU/kg BW. Blood samples are taken at various time points. Mouse samples are immuno-depleted with protein G sepharose (Invitrogen, Carlsbad, Calif.) prior to analysis in some experiments.

The methods of the invention include the diagnosis and testing effectiveness of a treatment for a disease or disorder associated with aberrant ADAMTS13 activity. Such diseases or disorders include thrombotic thrombocytopenic purpura (TTP or Moschcowitz disease). TTP is a rare disorder of the blood-coagulation system, causing extensive microscopic blood clots to form in the small blood vessels throughout the body. Most cases of TTP arise from deficiency or inhibition of the enzyme ADAMTS13, which is responsible for cleaving large multimers of VWF. Red blood cells passing the microscopic clots are subjected to shear stress which leads to hemolysis. Reduced blood flow and cellular injury results in end organ damage. Current therapy is based on support and plasmapheresis to reduce circulating antibodies against ADAMTS13 and replenish blood levels of the enzyme.

It has been found that subjects with congenital TTP or acquired TTP are severely deficient in ADAMTS13. ADAMTS13 is a metalloproteinase responsible for the breakdown of VWF, a protein that links platelets, blood clots, and the blood vessel wall in the process of blood coagulation. Very large VWF molecules are more prone to lead to coagulation. Hence, without proper cleavage of VWF by ADAMTS13, coagulation occurs at a higher rate, especially in the part of the blood vessel system where VWF is most active due to high shear stress: in the microvasculature. Congenital ADAMTS13 deficiency is caused by mutations of the ADAMTS13 gene. Subjects with the familial form have severe protease deficiency. ADAMTS13 gene mutation in familial TTP causes inactivity or decreased activity of ADAMTS13. Acquired deficiency occurs with the production of autoantibodies inhibiting ADAMTS13 activity. Acquired TTP is idiopathic and secondary to complications such as autoimmune disease, malignancy, stem cell transplantation, pregnancy (especially the third trimester), certain drugs (including ticlopidine, mitomycin, clopidogrel, and cyclosporine) or infection. The invention provides methods of measuring ADAMTS13 activity in blood and for testing effectiveness of treatment for diseases associated with abnormal ADAMTS13 levels or activity in the blood.

Deficiency of ADAMTS13 was originally discovered in Upshaw-Shulman syndrome, the recurring familial form of thrombotic thrombocytopenic purpura (TTP). By that time it was already suspected that TTP occurred in the autoimmune form as well, owing to its response to plasmapheresis and characterization of IgG inhibitors. Since the discovery of ADAMTS13, specific epitopes on its surface have been shown to be the target of inhibitory antibodies.

More than 70 mutations in the ADAMTS13 gene have been reported in people with the familial form of TTP. Most of these mutations change single amino acids in the ADAMTS13 enzyme. Other mutations lead to the production of an abnormally small version of ADAMTS13 that cannot function properly. Mutations in the ADAMTS13 gene severely reduce the activity of the ADAMTS13 enzyme. As a result, VWF is not processed normally in the bloodstream. If VWF is not processed normally by ADAMTS13, it promotes the formation of abnormal clots throughout the body by inducing platelets to stick together and adhere to the walls of blood vessels, even in the absence of injury. Additional factors such as pregnancy, diarrhea, surgery, and infection likely play a role in triggering abnormal clotting. Blood clots can block blood flow through small vessels, causing damage to the brain, kidneys, heart, and other organs. Abnormal clotting also causes other complications associated with TTP.

The TTP syndrome is characterized by microangiopathic hemolysis and platelet aggregation/hyaline thrombi whose formation is unrelated to coagulation system activity. Platelet microthrombi predominate; they form in the microcirculation (i.e., arterioles, capillaries) throughout the body causing partial occlusion of vessels. Organ ischemia, thrombocytopenia, and erythrocyte fragmentation (i.e., schistocytes) occur. The thrombi partially occlude the vascular lumina with overlying proliferative endothelial cells. The endothelia of the kidneys, brain, heart, pancreas, spleen, and adrenal glands are particularly vulnerable to TTP. The liver, lungs, gastrointestinal tract, gallbladder, skeletal muscles, retina, pituitary gland, ovaries, uterus, and testes are also affected to a lesser extent. No inflammatory changes occur.

In 1982, Moake and his colleagues observed ultra-large VWF (ULVWF) multimers in the plasma of four subjects with relapsing TTP (Moake J L, Semin. Hematol. 34:83-89, 1997; Moake J L, Semin. Hematol. 41:4-14, 2004). These multimers were the same size as those noted in the endothelial cells. The plasma of normal individuals has much smaller VWF. Moake suggested that there was a deficiency in an enzyme that reduces the large VWF to its normal size in plasma in subjects with TTP. Also noted was that this large VWF has a greater ability to adhere with platelets mediating a thrombus formation.

The present section provides a description of the relationship between the biological function of ADAMTS13 and the existence of ULVWF multimers and the occurrence of TTP or TTP-like clinical symptoms to the extent that such a description will facilitate a better understanding of the methods of the invention. There is a relationship between the biological function of ADAMTS13 and the existence of ULVWF multimers and the occurrence of TTP or TTP-like clinical symptoms. The pathogenesis of TTP is due to the platelet clumping in the microvasculature. There is an increased adherence of the ULVWF multimers leading to the formation of platelet thrombi due to the lack of a functioning proteolytic enzyme (ADAMTS13) to cleave these multimers.

TTP also may be related to cancer, chemotherapy, HIV infection, hormone replacement therapy and estrogens, and a number of commonly used medications (including ticlopidine, clopidogrel, and cyclosporine A). Systemic connective tissue diseases are other conditions besides TTP that are associated in some instances with low but detectable levels of ADAMTS13. Recombinant ADAMTS13 (rADAMTS13) is one of many therapies being tested in the treatment of TTP. The invention includes methods of testing the effectiveness of rADAMTS13 and all therapies associated with ADAMTS13-associated diseases.

A low level of ADAMTS13 causes clotting substances (platelets) in the blood to clump. As the platelets clump together, there are fewer platelets available in the bloodstream. This clumping, or aggregation, can lead to bleeding under the skin and purple-colored spots called purpura. It also can cause red blood cells to break apart (undergo hemolysis) as they are subjected to shear stress as they pass the microscopic platelet clots. Red blood cells are thus destroyed prematurely. Reduced blood flow and cellular injury results in end organ damage.

Levels of human ADAMTS13 antigen may be determined by ELISA (Rieger et al., *Thromb. Haemost.* 95:212-220, 2006). ADAMTS13 activity may be measured based on decreased collagen binding affinity of degraded VWF (Gerritsen et al., *Thromb. Haemost.* 82:1386-1389, 1999), which is a functional assay based on the preferential binding of high-molecular-weight forms of VWF to collagen. In this assay, the diluted plasma sample to be tested is added to normal plasma in which protease activity had been abolished. The VWF present in the protease-depleted plasma is digested by the VWF-cleaving protease in the test plasma. The proteolytic degradation leads to low-molecular-weight forms of VWF, which show impaired binding to microtiter plates coated with human collagen type III. The collagen-bound VWF is quantified using a peroxidase-conjugated rabbit antibody against human VWF. The values of VWF-cleaving protease activity in tested plasma samples are read from a calibration curve achieved by incubating the VWF-substrate with dilutions of a normal human plasma pool (NHP).

Current purpura or TTP therapy is based on support and plasmapheresis to reduce circulating antibodies against ADAMTS13 and replenish blood levels of ADAMTS13. Plasma exchange has been the first-line therapy for TTP since 1991. Congenital deficiency can replace the deficiency and mutations in the ADAMTS13 gene by plasma infusion. Acquired deficiency can remove the inhibitor of ADAMTS13 by plasmapheresis. However, plasma exchange is more effective treatment than plasma infusion. This life-threatening condition may have a positive outcome if recognized early and medical intervention is initiated early.

In addition, an increase in circulating levels of VWF and a decrease in ADAMTS13 activity in humans are considered risk factors for ischemic stroke (Zhao et al., American Society of Hematology, Abstract 259, Dec. 6-9, 2008, San Francisco, Calif.). Thus, the methods of measuring ADAMTS13 activity in vivo herein also have application in stroke diagnosis and therapy.

The invention also includes methods for diagnosing abnormal processing of VWF or deficiencies in ADAMTS13 concentration or activity, and testing therapies to increase ADAMTS13 concentration or activity used in the development of new therapies in the treatment of TTP and other ADAMTS13-related pathologies or disorders. In various aspects, other ADAMTS13-related pathologies or disorders include diseases which are characterized by abnormal levels of VWF or abnormal processing of VWF.

The present section provides a description of VWF syndrome to the extent that such a description will facilitate a better understanding of the methods of the invention. VWF syndrome manifests clinically when there is either an under-production or an overproduction of VWF. Overproduction of VWF causes increased thrombosis (formation of a clot or thrombus inside a blood vessel, obstructing the flow of blood) while reduced levels of, or lack of, high-molecular weight forms of VWF causes increased bleeding and an increased bleeding time due to inhibition of platelet aggregation and wound closure. The methods of the invention can be used in the diagnosis and treatment of various types of VWF syndrome.

A VWF deficiency may also cause a phenotypic Hemophilia A since VWF is an essential component of functional FVIII. In these instances, the half-life of Factor VIII is reduced to such an extent that its function in the blood coagulation cascade is impaired. Subjects suffering from VWD or VWF syndrome frequently exhibit an FVIII deficiency. In these subjects, reduced FVIII activity is not the consequence of a defect of the X chromosomal gene, but an indirect consequence of quantitative and qualitative change(s) of VWF in plasma. The differentiation between Hemophilia A and VWD may normally be effected by measuring the VWF antigen or by determining the ristocetin-cofactor activity. Ristocetin cofactor activity is measured by adding ristocetin and a platelet substrate to the subject's plasma. Ristocetin enhances binding of VWF to the platelet glycoprotein Ib receptor, resulting in agglutination. The subject's VWF will support the platelet agglutination induced by the ristocetin as measured by a change in light transmission. Therefore, this assay is an in vitro measurement of the functional activity of the subject's VWF. Both the VWF antigen content and the ristocetin cofactor activity are lowered in most VWD subjects, whereas they are normal in Hemophilia A subjects.

VWD is an inherited bleeding disorder that is caused by deficiency or dysfunction of VWF. Therefore, defects in VWF can cause bleeding by impairing platelet adhesion or by reducing the concentration of FVIII. VWD is diagnosed after a clinical and physical review, with personal and familial evidence of (primarily mucocutaneous) bleeding, and confirmed by laboratory testing. Laboratory testing typically entails initial plasma testing of factor VIII coagulant (FVIII:C), von Willebrand factor (VWF) protein (antigen; VWF:Ag), and VWF function or activity, which is assessed using the ristocetin cofactor (VWF:RCo) assay or the collagen binding assay (VWF:CBA). The VWF:CBA is based on measurement of the quantity of VWF bound to collagen, similar to the procedure for an enzyme-linked immunosorbent assay. Additional laboratory testing can comprise a battery of confirmatory and VWD subtype assisting assays, including assessment of VWF:multimers.

More specifically, the VWF:Ag assay is a quantitative assay and provides a measure of the overall level of VWF present in a patient's plasma; it is not a functional assay and yields no information concerning the quality of the VWF present. The VWF:CBA assay is a functional assay which provides information on the quality of VWF present. The VWF:Ag and VWF:CBA are complementary assays and, in various aspects, are used in combination. The VWF:RCo assay is both a quantitative and qualitative assay that provides information about the presence of VWF that lies between that provided individually by the VWF:Ag and VWF:CBA assays. The VWF:multimer assay is a qualitative procedure, and is semi-quantitative. The VWF:multimer assay provides a snap-shot of the VWF present. The above-described assays are well known in the art for testing VWF in vitro.

Methods provided also include, in various aspects, use of VWF. All forms of VWF and recombinant VWF are contemplated for use in the methods of the invention. In some aspects, VWF used in the methods of the invention include, but are not limited to: HUMATE-P®; and, IMMUNATE®, INNOBRAND®, and 8Y®.

In various aspects of the methods of the invention, recombinant VWF is administered to a subject. Recombinant VWF is administered at a dose of at least about 10 RCoU/kg BW, of at least about 20 RCoU/kg BW, of at least about 30 RCoU/kg BW, of at least about 40 RCoU/kg BW, of at least about 50 RCoU/kg BW, of at least about 60 RCoU/kg BW, of at least about 70 RCoU/kg BW, of at least about 80 RCoU/kg BW, of at least about 90 RCoU/kg BW, of at least about 100 RCoU/kg BW, of at least about 150 RCoU/kg BW, of at least about 200 RCoU/kg BW, of at least about 250 RCoU/kg BW, of at least about 300 RCoU/kg BW, of at least about 350 RCoU/kg BW, of at least about 400 RCoU/kg BW, of at least about 450 RCoU/kg BW, of at least about 500 RCoU/kg BW, of at least about 550 RCoU/kg BW, of at least about 600 RCoU/kg BW, of at least about 650 RCoU/kg BW, of at least about 700 RCoU/kg BW, of at least about 750 RCoU/kg BW, of at least about 800 RCoU/kg BW, of at least about 850 RCoU/kg BW, of at least about 900 RCoU/kg BW, of at least about 950 RCoU/kg BW, of at least about 1000 RCoU/kg BW, of at least about 1200 RCoU/kg BW, of at least about 1400 RCoU/kg BW, of at least about 1600 RCoU/kg BW, of at least about 1800 RCoU/kg BW, of at least about 2000 RCoU/kg BW, of at least about 2500 RCoU/kg BW, of at least about 3000 RCoU/kg BW, of at least about 3500 RCoU/kg BW, of at least about 4000 RCoU/kg BW, of at least about 4500 RCoU/kg BW, of at least about 5000 RCoU/kg BW, of at least about 6000 RCoU/kg BW, of at least about 7000 RCoU/kg BW, of at least about 8000 RCoU/kg BW, of at least about 9000 RCoU/kg BW, of at least about 10000 RCoU/kg BW, of at least about 20000 RCoU/kg BW, of at least about 50000 RCoU/kg BW, and of at least about 100000 RCoU/kg BW, and up to more than 100000 RCoU/kg BW.

In various other aspects of the methods of the invention, recombinant ADAMTS13 is administered to a subject. Recombinant human ADAMTS13 has been described (Plaimauer et al., *Blood* 100:3626-3632, 2002). Recombinant human ADAMTS13 is not yet available commercially for human administration, but the invention includes the use of such rADAMTS13 in clinical trials and when it is commercially available. In subjects with an inherited ADAMTS13 deficiency, normal human plasma is used as a source of ADAMTS13 and contains IU/mL of ADAMTS13. Purified plasma-derived or recombinant ADAMTS13 is currently available for use in animals at a dose range of 100-500 U/kg BW. The methods of the invention contemplate the use of any of these sources administered at an appropriate dose of IU/mL or U/kg BW. In one aspect, the invention includes the administration or rADAMTS13 at a dose of at least about 10 U/kg BW, of at least about 20 U/kg BW, of at least about 30 U/kg BW, of at least about 40 U/kg BW, of at least about 50 U/kg BW, of at least about 60 U/kg BW, of at least about 70 U/kg BW, of at least about 80 U/kg BW, of at least about 90 U/kg BW, of at least about 100 U/kg BW, of at least about 150 U/kg BW, of at least about 200 U/kg BW, of at least about 250 U/kg BW, of at least about 300 U/kg BW, of at least about 350 U/kg BW, of at least about 400 U/kg BW, of at least about 450 U/kg BW, of at least about 500 U/kg BW, of at least about 550 U/kg BW, of at least about 600 U/kg BW, of at least about 650 U/kg BW, of at least about 700 U/kg BW, of at least about 750 U/kg BW, of at least about 800 U/kg BW, of at least about 850 U/kg BW, of at least about 900 U/kg BW, of at least about 950 U/kg BW, of at least about 1000 U/kg BW, of at least about 1200 U/kg BW, of at least about 1400 U/kg BW, of at least about 1600 U/kg BW, of at least about 1800 U/kg BW, of at least about 2000 U/kg BW, of at least about 2500 U/kg BW, of at least about 3000 U/kg BW, of at least about 3500 U/kg BW, of at least about 4000 U/kg BW, of at least about 4500 U/kg BW, of at least about 5000 U/kg BW, of at least about 6000 U/kg BW, of at least about 7000 U/kg BW, of at least about 8000 U/kg BW, of at least about 9000 U/kg BW, of at least about 10000 U/kg BW, of at least about 20000 U/kg BW, of at least about 50000 U/kg BW, and of at least about 100000 U/kg BW, and up to more than 100000 U/kg BW.

In various aspects of the methods of the invention, the methods are carried out at a range of temperatures. In certain aspects, the invention includes methods comprising temperatures of about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 90° C., and about 100° C. In one aspect, the invention includes methods comprising temperatures of about 20° C. to about 40° C. In a particular aspect, the invention includes methods comprising temperatures of about 30° C. to about 35° C. In one aspect, the invention includes methods comprising a temperature of about 32° C.

In some aspects of the invention, the methods provided are carried out over a period of time. In various aspects, the invention includes methods comprising times of about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 25 minutes, about 30 minutes, about 35 minutes, about 40 minutes, about 45 minutes, about 50 minutes, about 55 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 36 hours, about 48 hours, about 72 hours, and about 96 hours. In certain aspects, the time ranges from about 10 seconds to about 3 hours. In particular aspects, the time ranges from about 30 seconds to about 1 hour. In more particular aspects the time ranges from about 15 minutes to about 30 minutes. In one aspect, the time is about 30 minutes. In another aspect, the time is about 15 minutes.

In some aspects, the methods provided are carried out under shear stress. In various aspects, the shear stress comprises a shear rate of about 100 s-1, about 200 s-1, about 300 s-1, about 400 s-1, about 500 s-1, about 600 s-1, about 700 s-1, about 800 s-1, about 900 s-1, about 1000 s-1, about 2000 s-1, about 3000 s-1, about 4000 s-1, about 5000 s-1, about 6000 s-1, about 7000 s-1, about 8000 s-1, about 9000 s-1, about 10,000 s-1, about 11,000 s-1, about 12,000 s-1, about 13,000 s-1, about 14,000 s-1, about 15,000 s-1, about 16,000 s-1, about 17,000 s-1, about 18,000 s-1, about 19,000 s-1, and about 20,000 s-1. In certain aspects, the shear stress comprises a shear rate of about 100 to about 10,000 s-1. In other aspects, the shear stress comprises a shear rate of about 1,000 s-1 to about 8,000 s-1. In one aspect, the shear rate is about 6,000 s-1.

In the methods provided, the rVWF or rADAMTS13 is administered to the mammal at any dose, including a variety of doses. The dosage may be based on body weight, activity of the VWF, activity of the ADAMTS13 protease, route of administration, health or condition of the mammalian recipient, and various factors as known to one of skill in the art.

EXAMPLES

Additional aspects and details of the invention will be apparent from the following examples, which are intended to be illustrative rather than limiting. Example 1 demonstrates that the susceptibility of human rVWF to ADAMTS13 cleavage varies among species. Example 2 shows the quantification and detection of ADAMTS13-derived cleavage products in plasma. Example 3 describes the detection of VWF cleavage fragments in plasma from subjects treated with human recombinant VWF. Example 4 describes the detection of VWF cleavage fragments after ADAMTS13-mediated VWF proteolysis under shear stress. Example 5 describes the detection of the effect of recombinant ADAMTS13 on endogenous VWF in plasma.

Example 1

Susceptibility of Human Recombinant Von Willebrand Factor to ADAMTS13 Cleavage Varies Among Species As set out herein above, VWF multimeric size and consequently VWF activity is regulated by ADAMTS13 activity in the blood. The aim of the study was to determine the susceptibility of human rVWF to cleavage by ADAMTS13 present in the plasma of different animal species. The ability of ADAMTS13 of different species to cleave human rVWF was tested in vitro as well as in vivo.

Determination of ADAMTS13 Activity: Diluted plasma samples from various animals were treated with barium chloride to activate ADAMTS13. Human rVWF (1 U/mL) (obtained) from CHO cells by fermentation and purification (Turecek et al., *Blood* 108: Abstract 1017, 2006; American Society of Hematology Annual Meeting Abstracts) was added and the mixture was incubated for 24 h under denaturing conditions (1.5 M urea). ADAMTS13 activity was then determined by a number of assays as described herein below.

Collagen Binding Activity (VWF:CBA) Assay: Samples were incubated in wells coated with collagen. Bound rVWF was detected using a polyclonal antihuman VWF antibody (DAKO, Denmark). The ADAMTS13 activity of plasma samples was expressed as a percent of residual VWF:CB activity compared to non-cleaved rVWF and data were illustrated in dose-response curves (1:20 to 1:3000 dilutions) or as a percent of collagen binding activity (CBA) decrease compared to normal human plasma (NHP) (1:20 dilution, equivalent to 50 mU/mL human ADAMTS13 activity). As described herein above, the VWF:CBA is a functional assay which provides quantitative as well as qualitative information on the quality of VWF present.

Fluorescence Resonance Energy Transfer (FRET) Activity Assay: The proteolytic activity of ADAMTS13 was measured using a fluorescent-labeled synthetic VWF peptide composed of 73 amino acids (FRETS-VWF73), Peptide Institute, Inc., Osaka, Japan) according to the manufacturer's instructions. Plasma samples (ADAMTS13 activity) were measured against a reference curve prepared from diluted normal human plasma (NHP) and expressed as a percent of NHP.

Sodium Dodecyl Sulfate-PolyAcrylamide Gel Electrophoresis (SDS-PAGE) and Immunoblottinq: SDS-PAGE was performed under reducing and non-reducing conditions using gradient (3%-8%) Tris-acetate gels followed by electro-blotting proteins onto PVDF membranes and incubating with monoclonal (MoAb. VW33-5: TaKaRa Bio Inc., Japan; MoAb N10: Abcam, USA, Kato et al. (2006) Transfusion, 46, 1444) and polyclonal rabbit anti-human VWF (DAKO, Denmark) antibodies. As a control, rVWF was treated with recombinant ADAMTS13 (Plaimauer et al., *Blood* 100: 3626, 2002). Secondary antibodies were labeled either with alkaline phosphatase (ALP) or horseradish peroxidase (HRP). The proteins were visualized using an ALP or enhanced chemiluminescence (ECL) detection kit. Multimer analysis was performed using high resolution horizontal SDS-agarose gel electrophoresis followed by immunostaining with a polyclonal rabbit anti-human VWF antibody.

Animals: Animal plasma samples used in this study were taken from monkey (Rhesus and Cynomolgus), rabbit (New Zealand White), pig (Yorkshire), dog (Beagle), guinea pig (Dunkin Hartley), rat (Sprague Dawley), and mice (VWF-deficient (def) and ADAMTS13-deficient (both with C57BL backgrounds).

In vivo studies: New Zealand White rabbits were treated with 1200 IU VWF:Ristocetin Cofactor activity (VWF:RCo)/kg body weight (BW) via intravenous injection. As described herein above, the VWF:RCo assay is one method of measuring VWF concentration/activity. Consequently, the concentration of VWF is often reported in VWF:RCo units. Blood samples before injection with rVWF and at various time points after injection were withdrawn from rabbits from the central auricular artery. Citrated plasma was prepared and stored frozen. Mice were either treated with 2000 IU VWF:RCo/kg BW alone or co-treated with rADAMTS13 at 19.4 µg/kg BW via intravenous injection. Blood samples from mice were withdrawn by cardiac puncture and citrated plasma was prepared and stored frozen. Mouse plasma samples from the in vivo studies were immunodepleted with protein G sepharose beads before loading gels to avoid reactivity of MoAbs with endogenous IgGs.

Cleavage of rVWF by Human ADAMTS13

The changes in multimeric structure of rVWF after cleavage by human ADAMTS13 are shown in FIG. 1. VWF multimers in normal human plasma (NHP) show satellite bands, as a result of ADAMTS13 cleavage (see FIG. 1A). Recombinant VWF contains high MW multimers without any satellite structure (see FIG. 1B). Incubation of rVWF with ADAMTS13 under denaturing conditions leads to the reduction of multimer numbers with appearance of lower multimers and satellite bands.

The specific cleavage of rVWF monomers by ADAMTS13 is shown in FIG. 2. ADAMTS13-specific cleavage of the rVWF monomers results in a 140 kDa N-terminal and a 176-kDa C-terminal fragment, which can be detected by immunoblotting. Results of immunoblotting using reducing SDS-PAGE with monoclonal antibodies for VWF are shown in FIG. 2A. Monoclonal antibody N10 detects the N-terminal 140-kDa fragment of VWF only when cleaved between $Tyr^{1605}$ and $Met^{1606}$ by ADAMTS13 (no reaction with the intact VWF). Monoclonal antibody VW33-5 detects the 176-kDa C-terminal fragment and the intact VWF. Results of immunoblotting using non-reducing SDS-PAGE with a polyclonal antibody for VWF are shown in FIG. 2B. The polyclonal rabbit anti-VWF Ab detects both cleavage fragments and the intact VWF multimers.

In Vitro Cleavage of rVWF by ADAMTS13 of Different Animal Species

Figure 3:
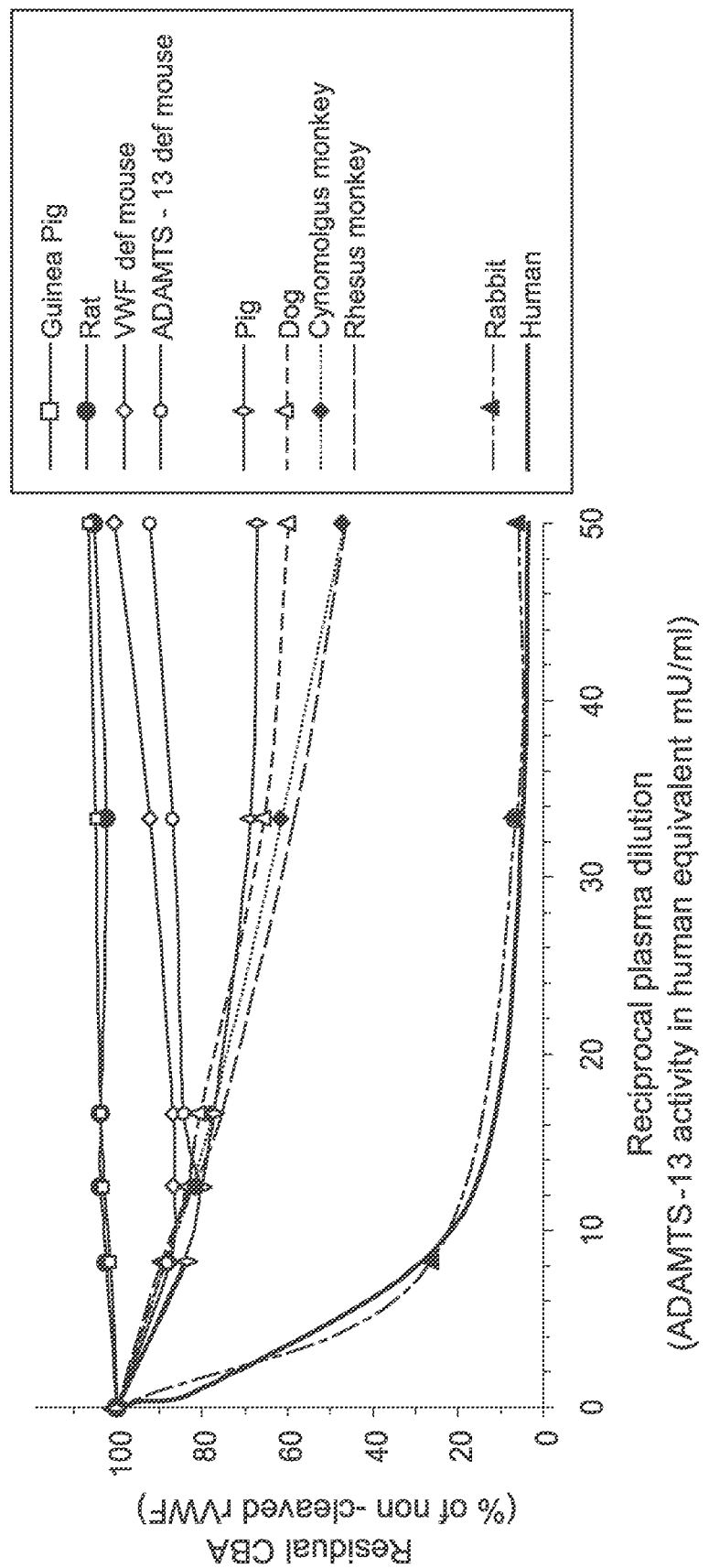
FIG. 3 shows ADAMTS13-dependent cleavage of rVWF detected by residual VWF:CBA assay.

ADAMTS13-dependent cleavage of rVWF was detected by residual VWF collagen-binding (VWF:CBA) activity (see FIG. 3). ADAMTS13 activity, as measured by FRETS and VWF:CBA, is also set out in FIG. 4. ADAMTS13 activity is expressed as a percentage of NHP. The enzymatic activity of ADAMTS13 in rabbit plasma was as high as that of human plasma (as measured by CBA and FRETS). Less ADAMTS13 activity was observed in samples from Cynomolgus and Rhesus monkeys, pig, and dog. However, FRETS showed higher ADAMTS13 activity than CBA. Little or no ADAMTS13 activity was detected in plasma samples derived from VWF-deficient mouse, ADAMTS13 deficient mouse, rat, and guinea pig.

Figure 5:
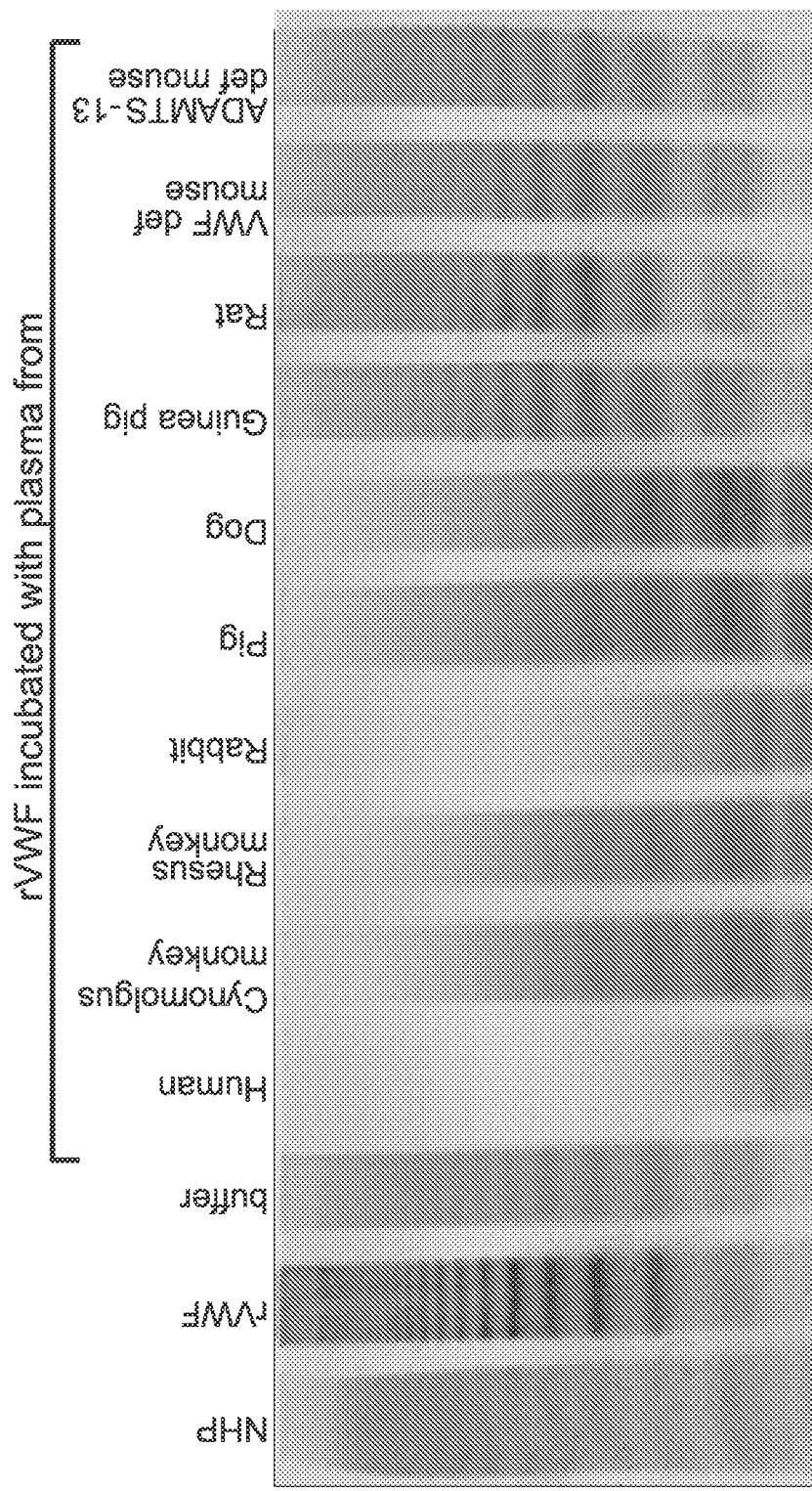
FIG. 5 illustrates VWF cleavage by ADAMTS13 using high resolution multimer analysis and demonstrates that rabbit plasma induced degradation of rVWF and the formation of satellite bands similar to human plasma.

Visualization of VWF cleavage by ADAMTS13 using high resolution multimer analysis (see FIG. 5) showed that rabbit plasma induced degradation of rVWF and the formation of satellite bands similar to normal human plasma (NHP). Cynomolgus monkey, Rhesus monkey, pig, and dog also showed specific cleavage of rVWF, however, to a lesser extent. No relevant changes were observed with guinea pig, rat, and mouse plasma compared with rVWF incubated with buffer.

Figure 6:
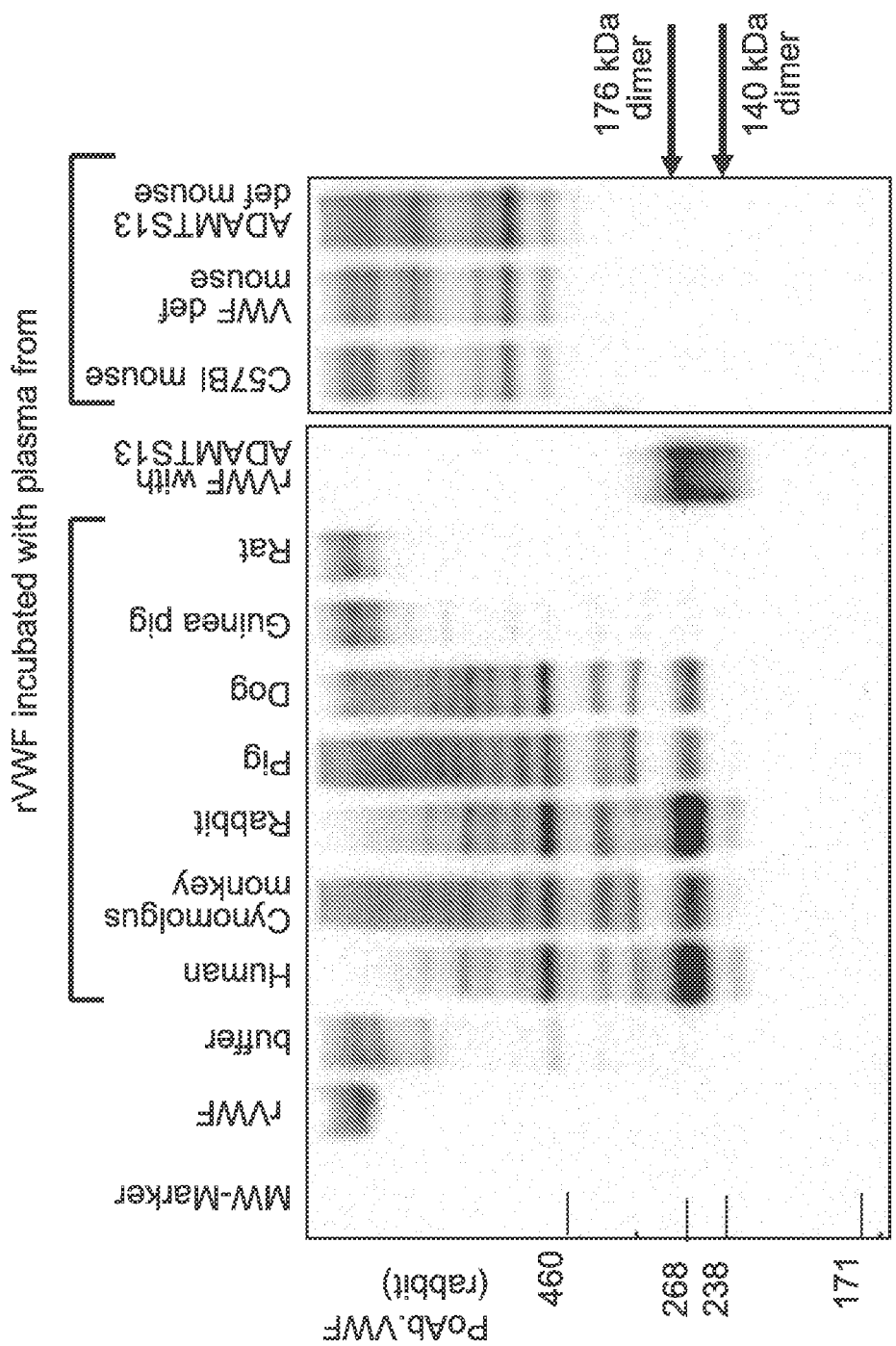
FIG. 6 shows the results of SDS-PAGE under non-reducing conditions followed by immunoblotting with polyclonal anti-human VWF antibody linked to HRP after rVWF was incubated with plasma from various animal species. The results indicated cleavage of human rVWF after incubation with plasma from human, rabbit, monkey, pig, or dog, but not with guinea pig, rat, or mouse.

The use of immunoblotting to visualize ADAMTS13 cleavage of rVWF (see FIGS. 6 and 7) demonstrated that the intensity of the bands (cleaved VWF) generally correlated well with the results of the VWF:CBA assay. FIG. 6 shows the results of SDS-PAGE under non-reducing conditions followed by immunoblotting with polyclonal anti-human VWF antibody linked with HRP. This polyclonal anti-human VWF antibody detects both VWF cleavage fragments (140 and 176 kDa) and the intact multimers, and is more sensitive but less specific than the monoclonal antibodies. The results of immunoblotting with the polyclonal antibody (see FIG. 6) indicated cleavage of human rVWF after incubation with plasma from human, rabbit, monkey, pig, or dog, but not with guinea pig, rat, or mouse.

Figure 7:
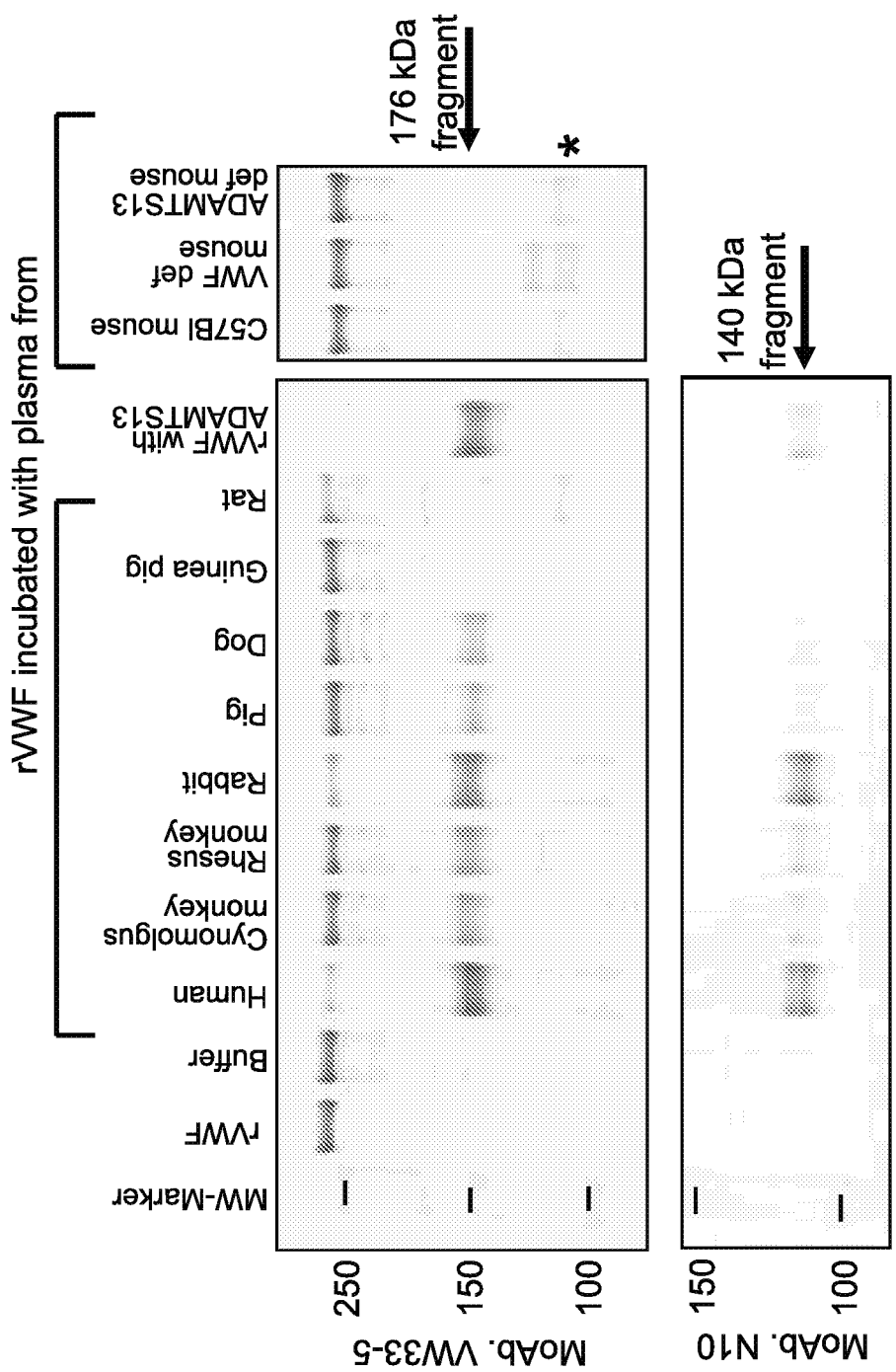
FIG. 7 shows the results of SDS-PAGE under reducing conditions followed by immunoblotting with monoclonal VWF antibodies. The asterisk denotes reactions of the goat anti-mouse IgG antibody (secondary) with endogenous mouse plasma IgGs.

A comparable result was obtained with the monoclonal antibody VW33-5 (see FIG. 7). FIG. 7 shows the results of SDS-PAGE under reducing conditions followed by immunoblotting with monoclonal VWF antibodies. As discussed herein above, monoclonal antibody VW33-5 detects the C-terminal 176 kDa fragment and the intact VWF, whereas monoclonal antibody N10 detects the N-terminal 140 kDa fragment of VWF, only when cleaved between $Tyr^{1605}$ and $Met^{1606}$ by ADAMTS13. ADAMTS13 cleavage of VWF was also detected by the N10 antibody (see 140 kDa bands in FIG. 7). The asterisk in FIG. 7 denotes reactions of the goat anti-mouse IgG antibody (secondary) with endogenous mouse plasma IgGs. These reactions precluded visualization of the 140 kDa monomer with the N10 antibody in the mouse samples. The intensity of the bands generally correlated well with results from CBA assays.

In plasma of human, rabbit, Cynomolgus and Rhesus monkeys, ADAMTS13-specific cleavage of the rVWF monomers was demonstrated by immunoblotting. In pig and dog, low levels of the 176 kDa fragment were detectable. No rVWF fragments were visible when incubated with plasma of C57BL mouse strains, rat, and guinea pig.

In Vivo Cleavage of rVWF by ADAMTS13 of Different Animal Species

Specific in vivo cleavage of rVWF (1200 I U VWF:RCo/kg) by ADAMTS13 (140 kDa and 176 kDa fragments) in rabbits was detected with monoclonal antibodies by immunoblotting after reducing SDS-PAGE (see FIGS. 8A and B). As controls, uncleaved rVWF and rVWF cleaved with rADAMTS13 in vitro are shown. Characteristic changes in multimer pattern shortly after rVWF administration are also seen (see FIG. 8C).

Figure 9A:
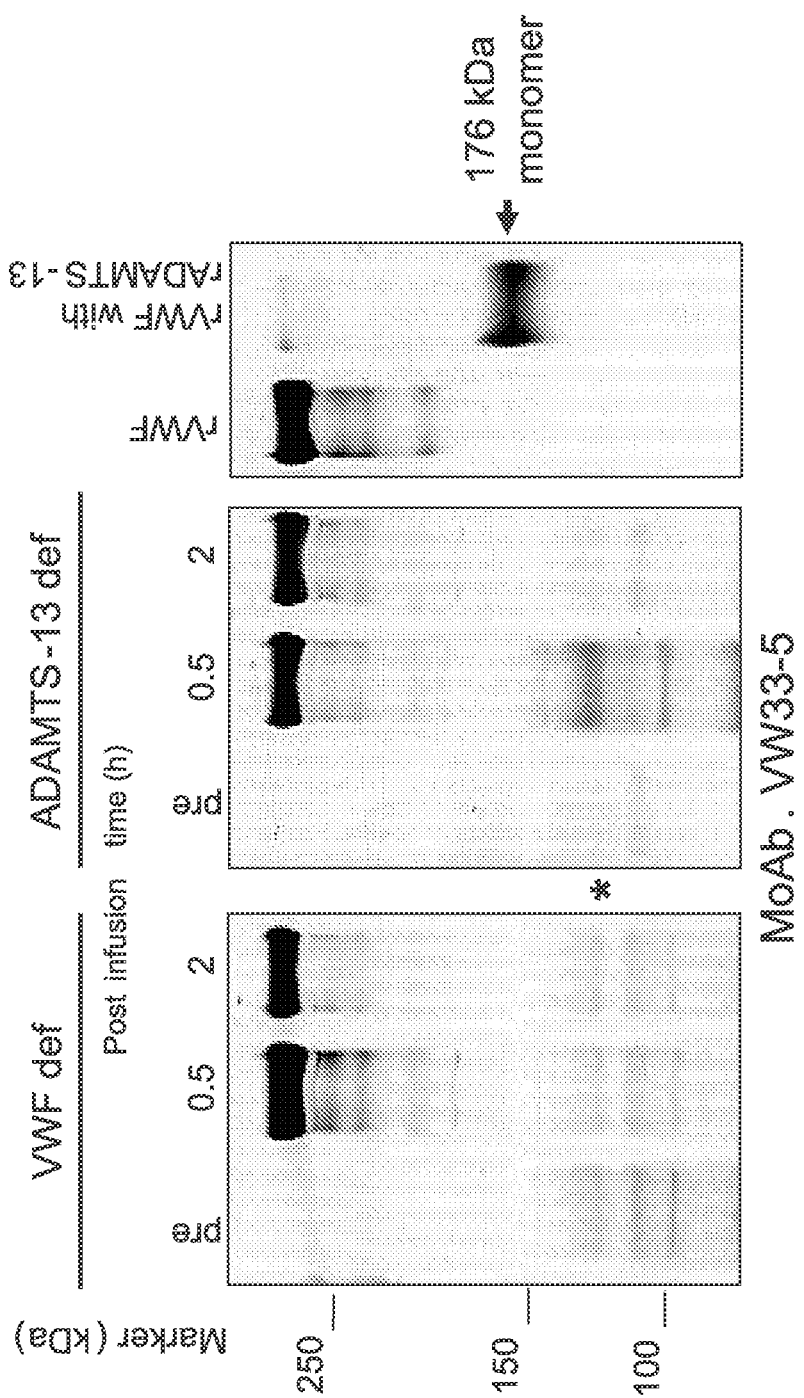
FIGS. 9A, 9B and 9C show specific in vivo cleavage of rVWF (2000 IU VWF:RCo/kg) by ADAMTS13 in VWF-deficient and ADAMTS13-deficient mice. The 176 kDa VWF cleavage fragment was not visible in either mouse strain using the monoclonal antibody specific to the C-terminal fragment (FIG. 9A). The asterisk denotes reactions of the goat anti-mouse IgG antibody with mouse plasma IgGs. No detectable changes in rVWF multimer pattern were observed (FIG. 9B). 140 kDa and 176 kDa homodimers were only detectable in VWF-deficient, but not in ADAMTS13-deficient mice using the more sensitive (but less specific) polyclonal antibody under non-reducing conditions (FIG. 9C).
Figure 9B:
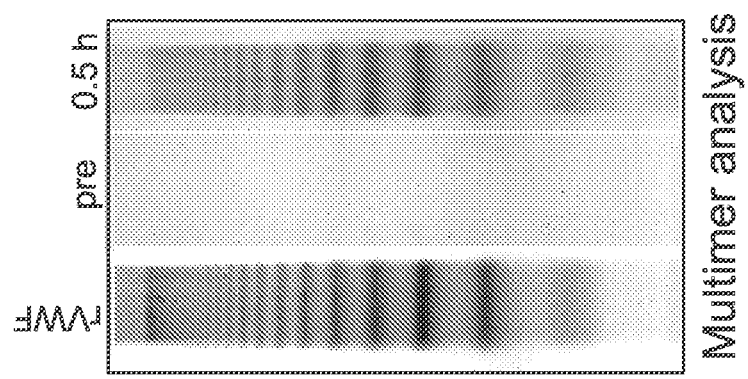
Figure 9C:
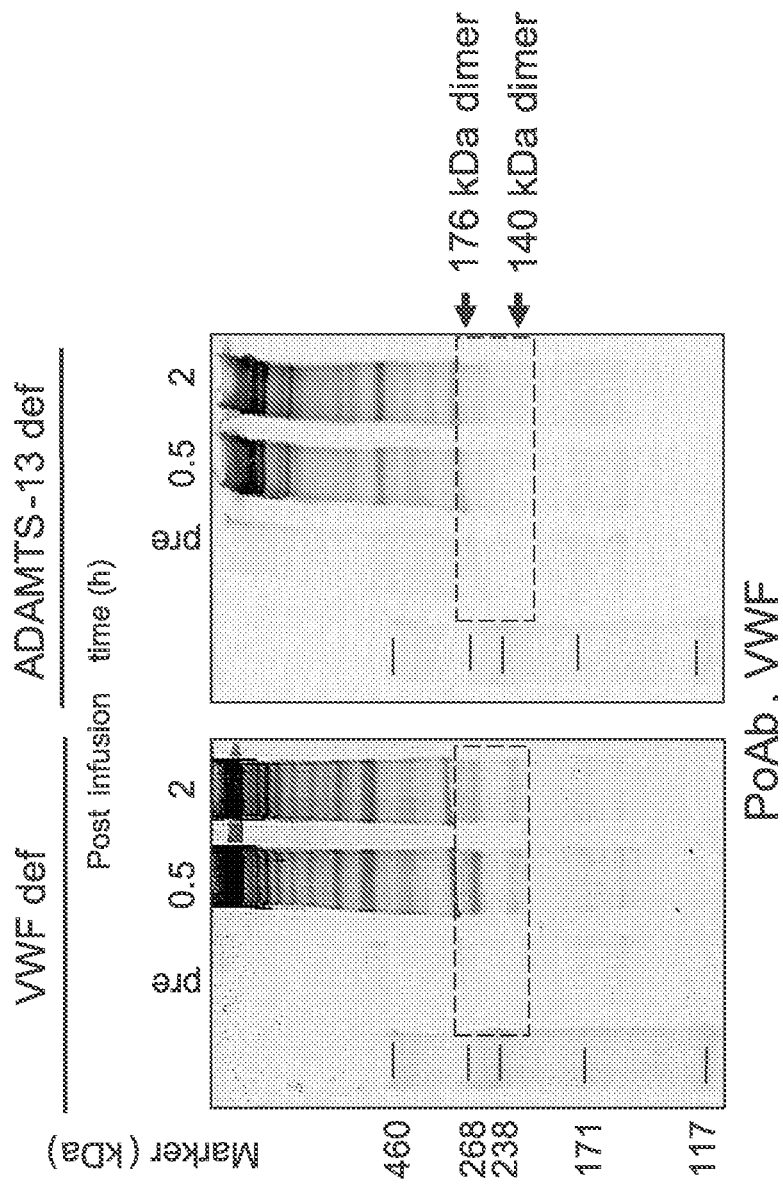

FIG. 9 shows specific in vivo cleavage of rVWF (2000 IU VWF:RCo/kg) by ADAMTS13 in VWF-deficient and ADAMTS13-deficient mice. The 176 kDa VWF cleavage fragment was not visible in either mouse strain using the monoclonal antibody specific to the C-terminal fragment (VW33-5) (FIG. 9A) after non-reducing SDS-PAGE. The asterisk denotes reactions of the goat anti-mouse IgG antibody with mouse plasma IgGs. These reactions precluded visualization of the 140 kDa monomer with the N10 antibody. No detectable changes in rVWF multimer pattern were observed (FIG. 9B). 140 kDa and 176 kDa homodimers were only detectable in VWF-deficient, but not in ADAMTS13-deficient mice using the more sensitive (but less specific) polyclonal antibody under non-reducing conditions (FIG. 9C).

Figure 10:
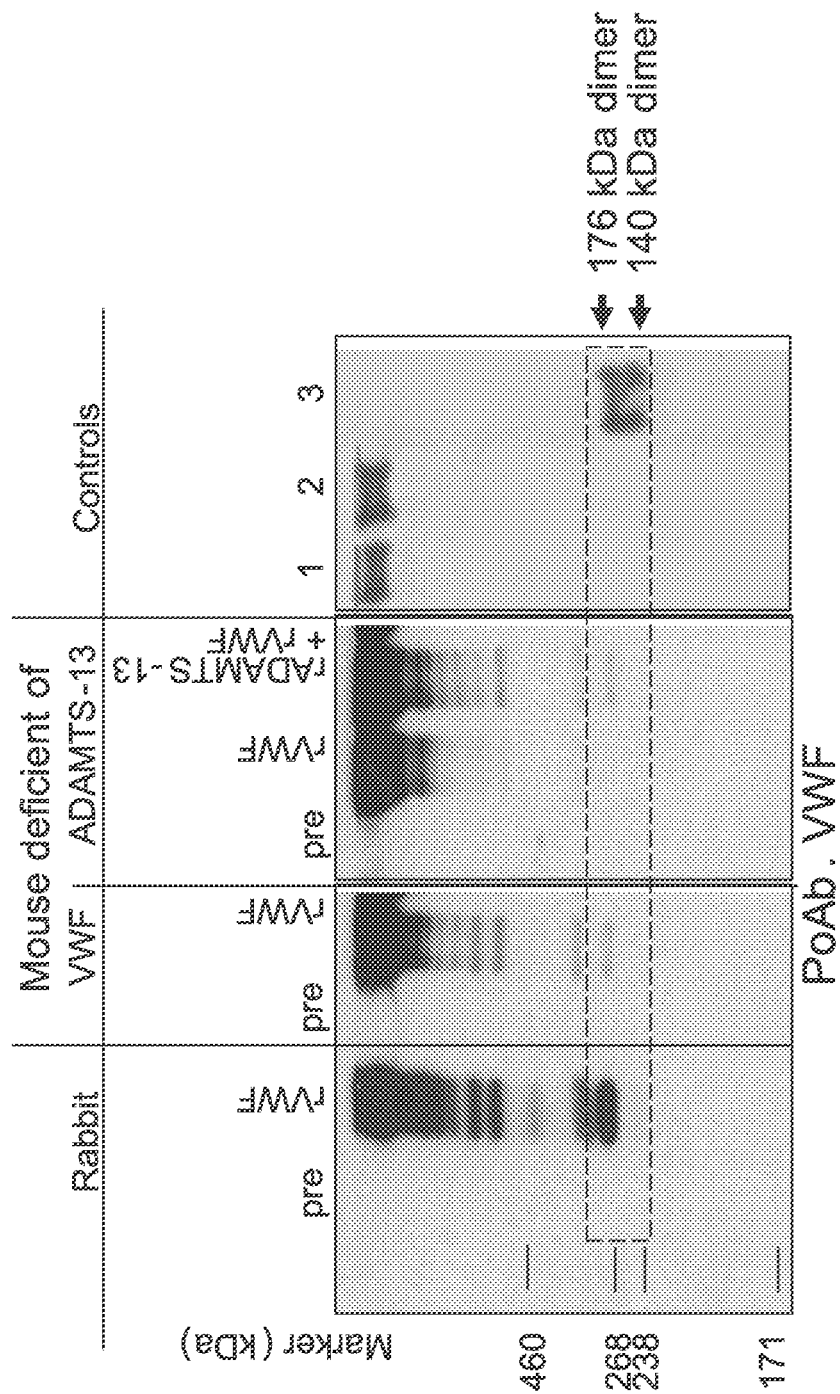
FIG. 10 shows a direct comparison of the efficiency of ADAMTS13 cleavage in various animal models using non-reducing SDS-PAGE after equal amounts of VWF:Ag were loaded. In rabbit plasma samples, a stronger band corresponding to the 176 kDa VWF cleavage product was detectable compared to the VWF-deficient mouse sample. No cleavage was detectable in ADAMTS13-deficient mouse plasma. Co-injection of rVWF with human rADAMTS13 induced cleavage of rVWF.

A direct comparison of the efficiency of ADAMTS13 cleavage in the animal models was carried out under non-reducing SDS-PAGE with equal amounts of VWF:Ag being loaded (see FIG. 10). In rabbit plasma samples, a stronger band corresponding to the 176 kDa VWF cleavage product was detectable compared to the VWF-deficient mouse sample. No cleavage was detectable in ADAMTS13-deficient mouse plasma. Co-injection of rVWF with human rADAMTS13 induced cleavage of rVWF. Control lanes 1-3 in FIG. 10 represent rVWF uncleaved (1), rVWF premixed with rADAMTS13 (2), and rVWF cleaved in vitro by rADAMTS13 (3).

Figures 11A, 11B:
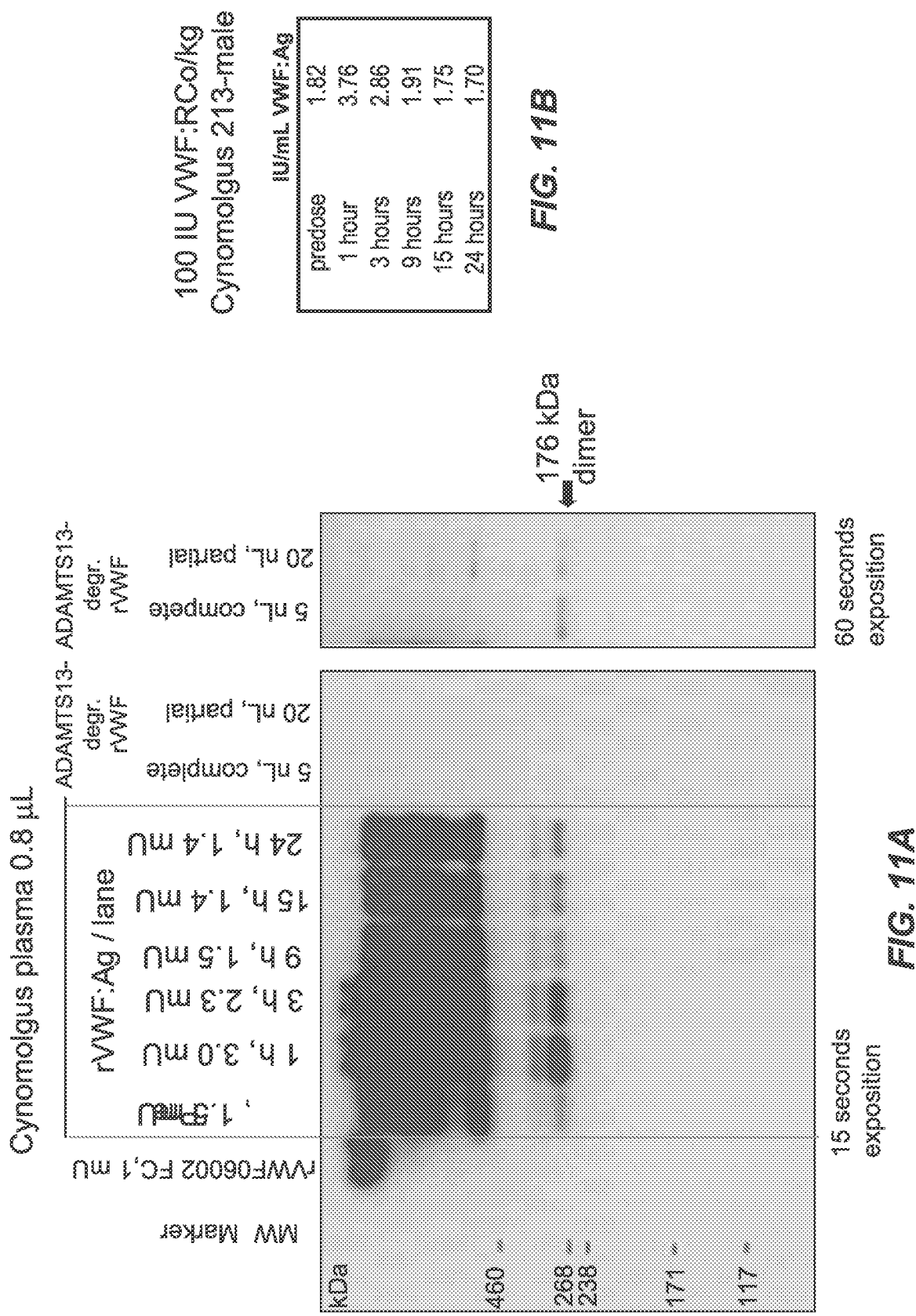
FIGS. 11A-11B show results of Western blot detection of VWF cleavage fragments in Cynomolgus plasma after a single dose injection of rVWF (100 IU/kg). Completely and partially ADAMTS13-degraded rVWF fragments (1 Ag U/mL) were measured in Cynomolgus plasma after a single dose injection of rVWF after 15 seconds of exposure (FIG. 11A) with the rabbit anti-human VWF antibody. The intensity of a 176 kDa dimer band increased after injection of rVWF. The 176 kDa VWF dimer was greater than baseline (pre-injection) even 24 h after VWF injection (FIG. 11A), when no elevated VWF antigen (VWF:Ag) was measured (FIG. 11B).

VWF cleavage fragments were detected in Cynomolgus plasma after a single dose injection of rVWF (100 IU/kg) (see FIG. 11). Completely and partially ADAMTS13-degraded rVWF fragments (1 Ag U/mL) were measured in Cynomolgus plasma after a single dose injection of rVWF with Western blotting under non-reducing conditions after 15 seconds of exposure with the rabbit anti-human VWF antibody (FIG. 11A). A baseline degradation band (176 kDa dimer) was seen in Cynomolgus plasma before rVWF injection. An increase in the amount of the 176 kDa VWF dimer was seen after the injection of rVWF. The 176 kDa VWF dimer was greater than baseline (pre-injection) even 24 h after VWF injection (FIG. 13A), when no elevated VWF antigen (VWF:Ag) was measured (FIG. 11B).

These results show that substantial differences in the in vitro cleavage susceptibility of human rVWF by ADAMTS13 were found among the plasma of different animal species. Rabbit plasma was as effective in proteolysis of human rVWF as homologous human plasma. Plasma samples from Cynomolgus monkey, Rhesus monkey, pig, and dog showed medium ADAMTS13 proteolytic activity toward human rVWF. Plasma samples from VWF-deficient mouse, rat, and guinea pig showed virtually no ADAMTS13 activity towards human rVWF.

The in vivo studies with injection of high doses of rVWF in rabbits and mice confirmed the in vitro results. The residual cleavage observed in the VWF-deficient mouse was confirmed by the absence of cleavage in the ADAMTS13-deficient mouse. In rabbit plasma, rVWF was efficiently cleaved as demonstrated by ADAMTS13-specific cleavage fragments of VWF and satellite band formation of multimers. In VWF-deficient and ADAMTS13-deficient mouse plasma, hardly any rVWF cleavage was noted. Human rADAMTS13 was able to substitute for the mouse ADAMTS13 enzyme and cleave VWF when co-injected with rVWF in mice.

These data demonstrate poor species compatibility between human rVWF and endogenous ADAMTS13 present in plasma of mice, rats, and guinea pigs. ADAMTS13 present in the plasma of the Cynomolgus monkey, Rhesus monkey, pig, and dog showed better proteolytic activity toward human rVWF; however ADAMTS13 proteolytic activity was still lower than that of human ADAMTS13 activity toward human rVWF. Rabbit ADAMTS13 activity appeared to be as effective in proteolysis of human rVWF as homologous human plasma. These species differences in the proteolytic activity/specificity of ADAMTS13 should be taken into consideration when evaluating the efficacy, (patho)physiology, and metabolism of human rVWF in different animals. This study also suggests that the rabbit, and rabbit plasma in general, may be useful as a model for evaluating and testing human rVWF.

The method is also suitable for detecting the effect of endogenous ADAMTS13 on injected rVWF in various animal models. The methods of the invention allow for the investigation of the suitability of various animal models in determining the effect of ADAMTS13 on rVWF in different species.

Example 2

Quantification and Detection of ADAMTS13-derived Cleavage Products in Plasma

The aim of the study was to develop an assay to determine if ADAMTS13-mediated cleavage of VWF (i.e., VWF fragments) could be detected in plasma samples of Type III VWD subjects after treatment with rVWF during a clinical study.

Normal human plasma, severe VWF-deficient human plasma, ADAMTS13-deficient human plasma, and Cynomolgus plasma samples, obtained before and after (1, 3, 9, 15, and 24 hours) rVWF injection (100 IU VWF:RCo/kg), were used. Completely and partially degraded rVWF treated with rADAMTS13 under denaturing conditions were used as controls.

Plasma samples were applied to SDS-PAGE under non-reducing conditions followed by Western blotting. The blots were stained with an HRP-labeled rabbit anti-human VWF polyclonal antibody (Dako), and developed with an enhanced chemiluminescence (ECL) plus technique.

Completely and partially ADAMTS13-degraded rVWF (1 Ag U/mL) were measured in buffer and VWF-deficient plasma with Western blotting under non-reducing conditions after 15 seconds of exposure with the polyclonal rabbit anti-human VWF antibody (see FIG. 12). Reducing conditions were not sensitive enough to visualize results. No differences between dilutions in buffer (FIG. 12A) and VWF-deficient plasma (FIG. 12B) were detected with Western blot analysis. The VWF-derived C-terminal fragment (176 kDa dimer) was detected using ECL. Completely degraded rVWF (1 Ag U/mL) could be detected at >62.5 fold dilution (16 nL/µL plasma). No cross reaction was seen with other human plasma proteins.

Figure 13B:
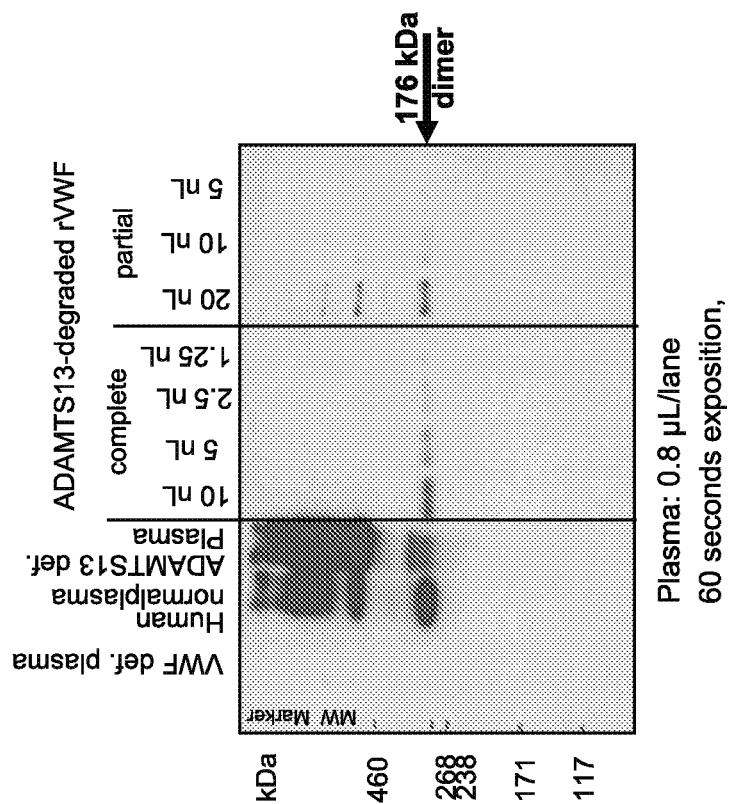
FIGS. 13A-13B show that VWF cleavage fragments were detected in plasma by increasing the sensitivity of the assay by increasing exposure time. Completely and partially ADAMTS13-degraded rVWF (1 Ag U/mL) were measured in buffer and VWF-deficient plasma with Western blotting under non-reducing conditions after 15 seconds (FIG. 13A) and 60 seconds (FIG. 13B) of exposure with the rabbit anti-human VWF antibody.
Figure 13A:
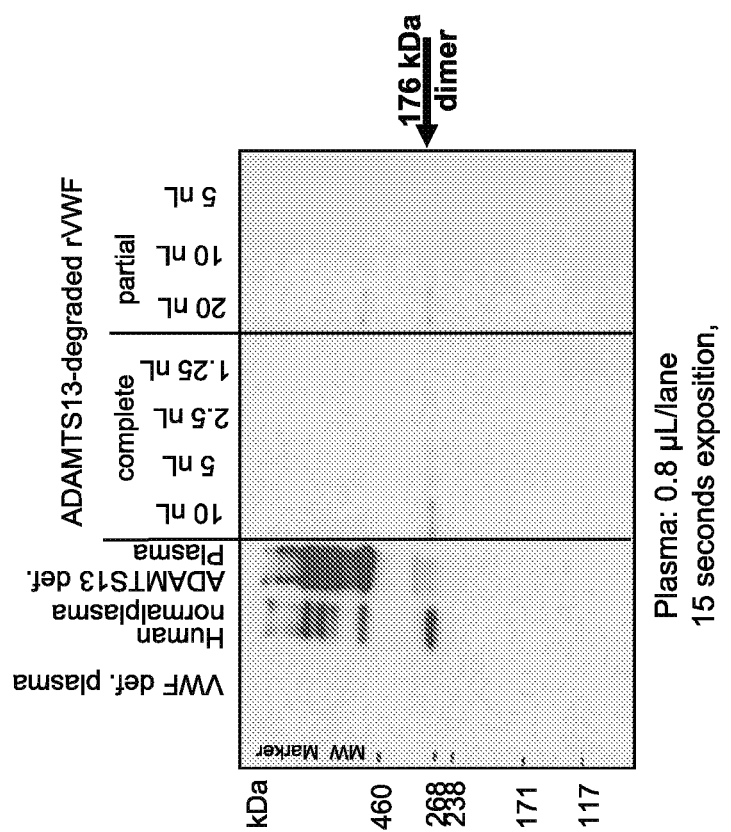

VWF cleavage fragments were detected in plasma by increasing the sensitivity of the assay through increasing the exposure time (see FIG. 13). Completely and partially ADAMTS13-degraded rVWF (1 Ag U/mL) were measured in buffer and VWF-deficient plasma with Western blotting under non-reducing conditions after 15 seconds (FIG. 13A) and 60 seconds (FIG. 13B) of exposure with the rabbit anti-human VWF antibody. A 176 kDa cleavage fragment can be seen in normal human plasma, but not in VWF-deficient plasma (see FIGS. 13A and B). Traces of a 176 kDa cleavage fragment are detected in ADAMTS13-deficient plasma (see FIGS. 13A and B), but in a much lesser amount compared to the total VWF present. Completely degraded rVWF (1 Ag U/mL) was well detected at up to 320 times dilution (2.5 nL/0.8 µL plasma/lane) with 60 sec exposure time (see FIG. 13B).

Figures 14A, 14B:
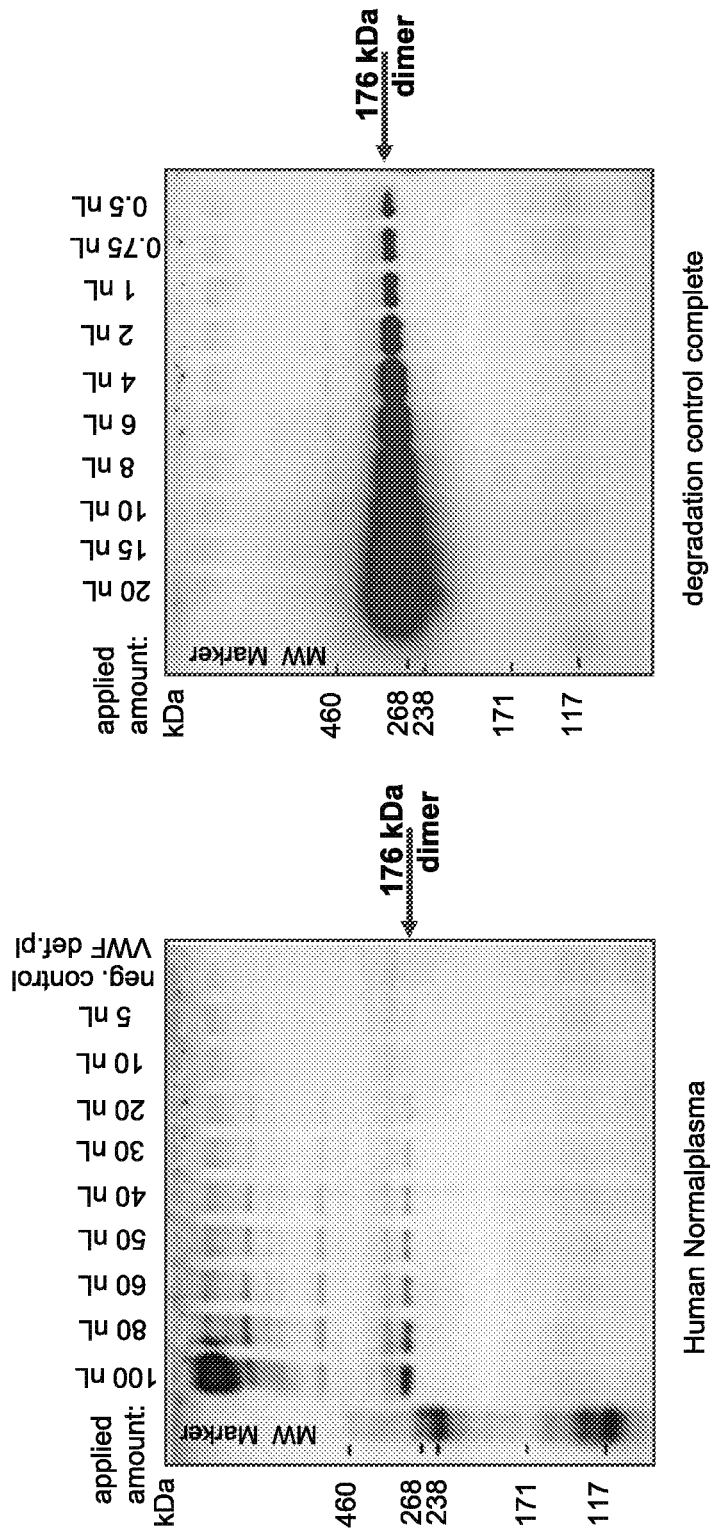
FIGS. 14A-14B show results of optimizing sensitivity of Western blot analysis by carrying out sample dilutions and increasing blot exposure times. Normal human plasma was diluted 20-fold and a 176 kDa cleavage product was well detected after a two minute exposure time in 20-40 nL normal human plasma (FIG. 14A). No ADAMTS13-specific band (VWF cleavage product) could be seen in VWF-deficient plasma (FIG. 14A). Fully degraded rVWF (1 Ag U/mL) was diluted 40-fold (0.5 nL to 20 nL) and could be detected at a level of sensitivity of about 0.0006 U/mL (0.5 nL/0.8 µL plasma) (FIG. 14B).

The detection limit or level of sensitivity of the Western blot assay was further determined by diluting plasma samples and increasing exposure time to two minutes (FIG. 14). Normal human plasma was diluted 20-fold (from 5 nL to 100 nL) and a 176 kDa cleavage product was well detected after two minutes when 20-40 nL normal human plasma was applied (in 0.8 µL VWF-deficient plasma) (0.025-0.05 Ag U/mL VWF) (see FIG. 14A). No ADAMTS13-specific band (VWF cleavage product) could be seen in VWF-deficient plasma (FIG. 14A). Fully degraded rVWF (1 Ag U/mL) was diluted 40-fold (0.5 nL to 20 nL) and could be detected, as measured by the 176 kDa VWF dimer, at about 0.0006 U/mL concentration (0.5 nL/0.8 µL plasma) (see FIG. 14B).

Figures 15A, 15B:
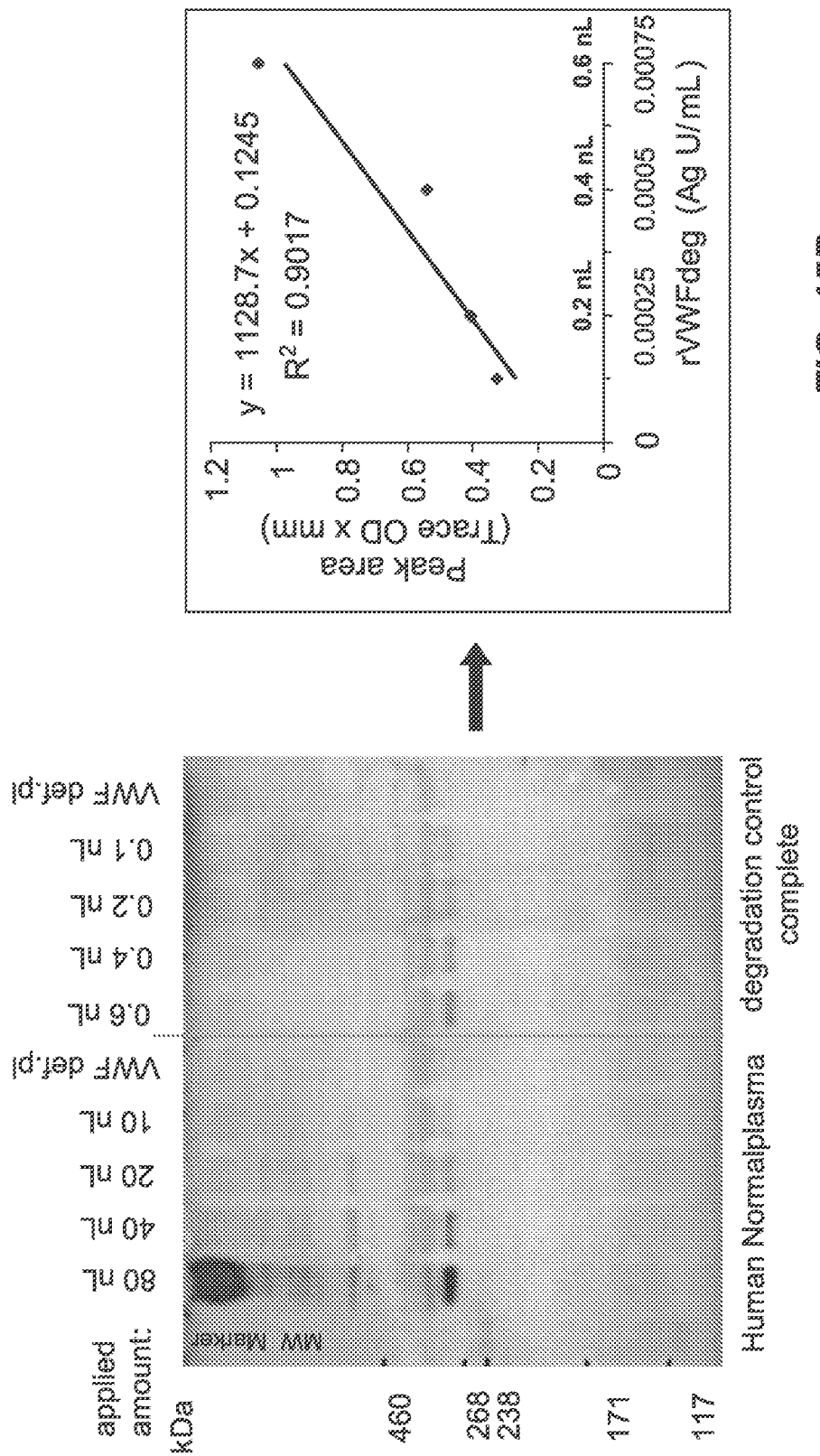
FIGS. 15A-15B show the quantification of VWF cleavage by ADAMTS13 in plasma. A 176 kDa VWF cleavage product was well detected in normal human plasma (about 0.025 Ag U/mL VWF) (FIG. 15A). Approximately 1-2% of C-terminal dimers (the 176 kDa ADAMTS13-specific cleavage product) were found in human normal plasma when calculated from a reference curve (FIG. 15B) constructed from the band intensity of different amounts of completely degraded rVWF (1 Ag U/mL).

VWF cleavage by ADAMTS13 was further measured in plasma by quantifying VWF degradation bands (FIG. 15). A 176 kDa VWF cleavage product was well detected in normal human plasma at 20 nL applied in 0.8 µL of VWF-deficient plasma (0.025 Ag U/mL VWF) (see FIG. 15A). Approximately 1-2% of C-terminal dimers (the 176 kDa ADAMTS13 specific cleavage product) were found in human normal plasma when calculated from a reference curve constructed from the band intensity of the different amounts of completely degraded rVWF (1 Ag U/mL) (see FIG. 15B).

Therefore, a highly sensitive method for the specific detection of ADAMTS13-mediated VWF cleavage bands in plasma was developed. Based on a quantitative comparison with a completely degraded rVWF, approximately 1-2% of total VWF:Ag appeared as a 176 kDa degradation band in normal human plasma. C-terminal dimers (176 kDa dimers) in normal plasma can be detected at a lower limit of 0.025-0.05 U/mL VWF:Ag concentration.

This study showed that the VWF cleavage product correlates with ADAMTS13 activity indicating that this method is suitable for detecting the effect of endogenous ADAMTS13 on injected rVWF in vivo. The method can also be used as a marker of in vivo ADAMTS13 activity. This example therefore illustrates the development of a highly sensitive method for measuring ADAMTS13 activity in vivo by the examination of VWF cleavage products in plasma samples.

Example 3

Detection of VWF Cleavage Fragments in Plasma from Subjects Before and After Treatment with RVWF In the course of a clinical phase I trial, type III VWD subjects were treated with 7.5 IU VWF:RCo/kg body weight of rVWF. Blood samples were collected before the treatment and at various time points after the treatment up until 96 h and assayed for the presence of ADAMTS13-dependent VWF cleavage fragments.

Figure 16A:
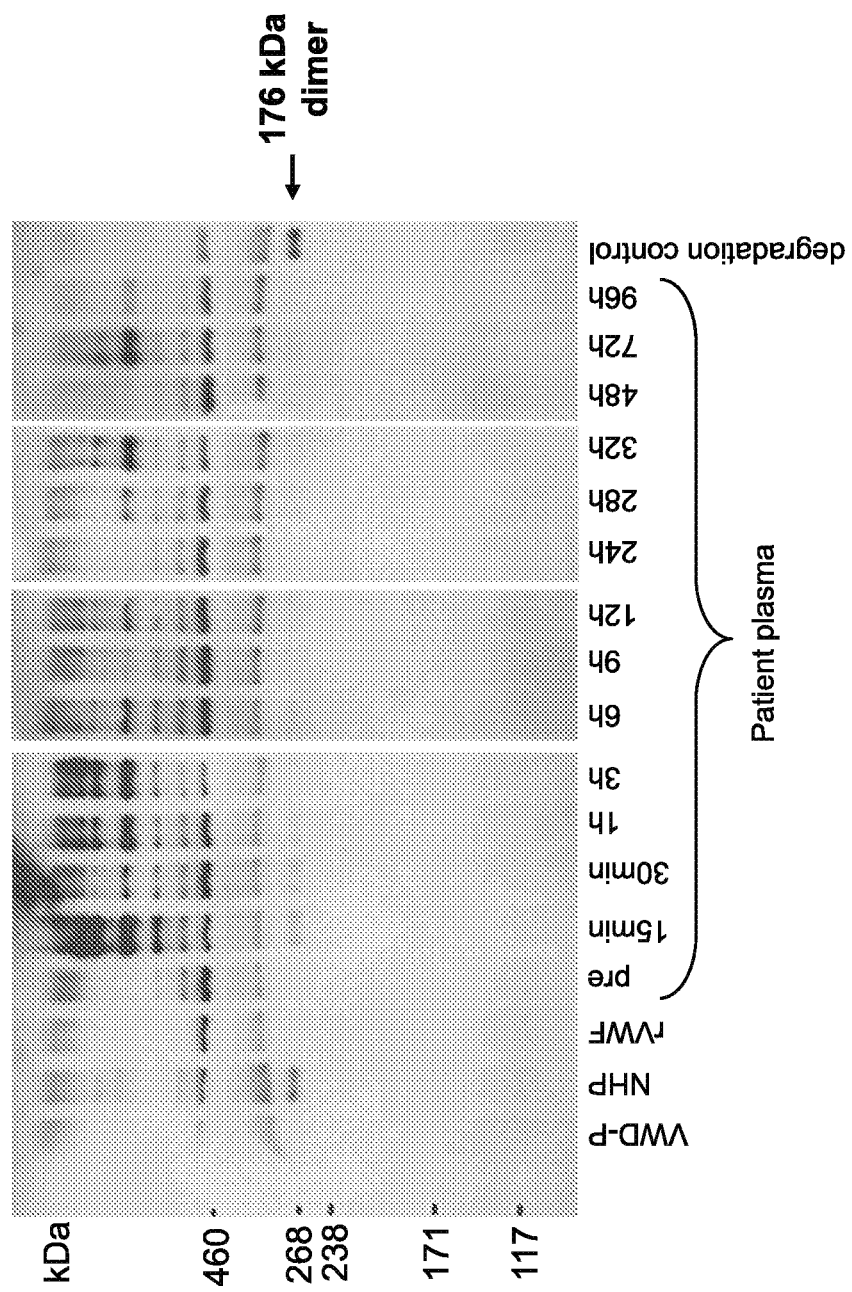
FIGS. 16A-16B show the results of Western blot detection of the C-terminal VWF cleavage fragment in human plasma after administration of 7.5 (FIG. 16A) and 20 (FIG. 16B) IU VWF:RCo/kg to subjects in a clinical phase I trial. The ADAMTS13-dependent rVWF fragment was detectable in plasma with the rabbit anti-human VWF antibody already 15 minutes post-treatment. The intensity of the 176 kDa dimer band remained above background for approximately 1 hour (7.5 IU rVWF) and 32 hours (20 IU rVWF).

The respective plasma samples were applied to SDS-PAGE under non-reducing conditions on 3-8% Tris-Acetate gels (500 nL per lane) followed by Western blotting using an HRP-labeled rabbit anti-human VWF polyclonal antibody (Dako) in combination with an ECL plus technique. VWD plasma (VWD-P, George King), normal human plasma (0.1 U/ml diluted in VWD plasma, NHP), rVWF (0.1 U/ml diluted in VWD plasma), and in vitro digested rVWF (1 nL diluted in VWD plasma, degradation control) served as controls. The 176 kDa dimer was not detectable in the pre-treatment sample, but was clearly discernible in the post-treatment samples of the 15 min, 30 min, and 1 h time points (see FIG. 16A). As this fragment was absent from the rVWF, the subject's endogenous ADAMTS13 must have cleaved the administered rVWF.

In the course of a clinical phase I trial, type III VWD subjects were treated with 20 IU VWF:RCo/kg body weight of rVWF (a greater dose than set out above). Blood samples were collected before the treatment and at various time points after the treatment up until 96 h and assayed for the presence of ADAMTS13-dependent VWF cleavage fragments.

Figure 16B:
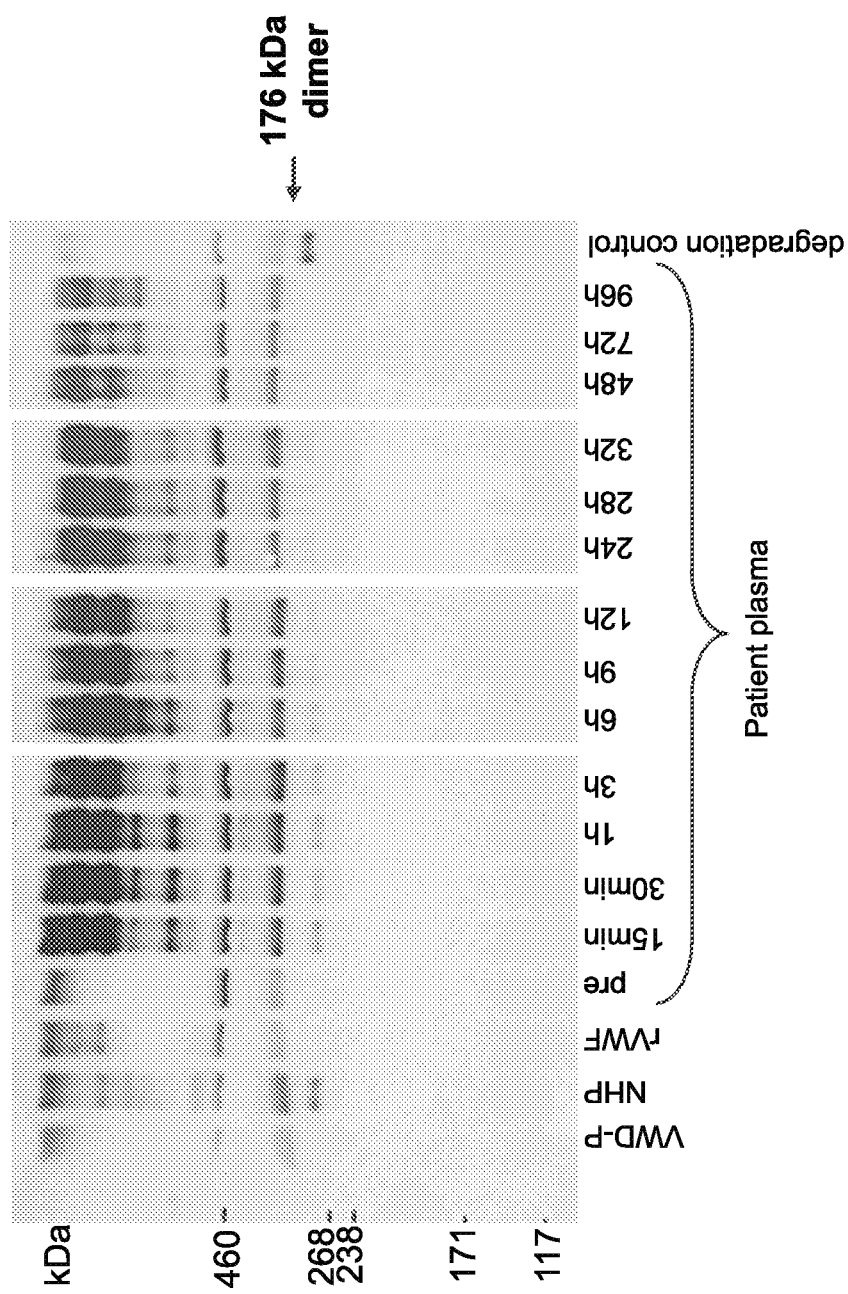

The respective plasma samples were applied to SDS-PAGE under non-reducing conditions as described above. The 176 kDa dimer was not detectable in the pre-treatment sample, but was clearly discernible in the post-treatment samples up to the 32 h time point (see FIG. 16B). The ADAMTS13-specific cleavage fragment was discernible in plasma by Western blotting for a longer time because of the greater dose of rVWF (20 vs. 7.5 IU/kg) administered.

Example 4

Detection of VWF Cleavage Fragments after ADAMTS13-mediated VWF Proteolysis under Shear Stress Shear-induced proteolytic cleavage of VWF was performed in a cone-plate viscometer (HAAKE Rheo Stress 1, Thermo Fisher Scientific, Waltham, Mass., USA) in a total volume of 500 μL using a 60 mm cone (0.5° angle). The experimental design was based on a publication by Shim et al. (*Blood* 111:651-657, 2008). rVWF (1 IU/mL final concentration) was mixed with rADAMTS13, plasma-derived ADAMTS13 (pADAMTS13), or normal human plasma (0.2 U/mL final concentration) in a reaction buffer containing 50 mM HEPES, 150 mM NaCl, 0.1 μM $ZnCl_2$, and 5 mM $CaCl_2$, pH=7.4. The reaction was started by subjecting the samples to a shear rate of 6000 $s^{-1}$ at 37° C. for 15 minutes and was stopped by the addition of EDTA (5 mM final concentration). As a negative control, identical samples were similarly incubated in the absence of shear stress. As a positive control, rVWF was incubated with rADAMTS13 under denaturing conditions (1.5 M urea) for 24 hours.

Figure 17:
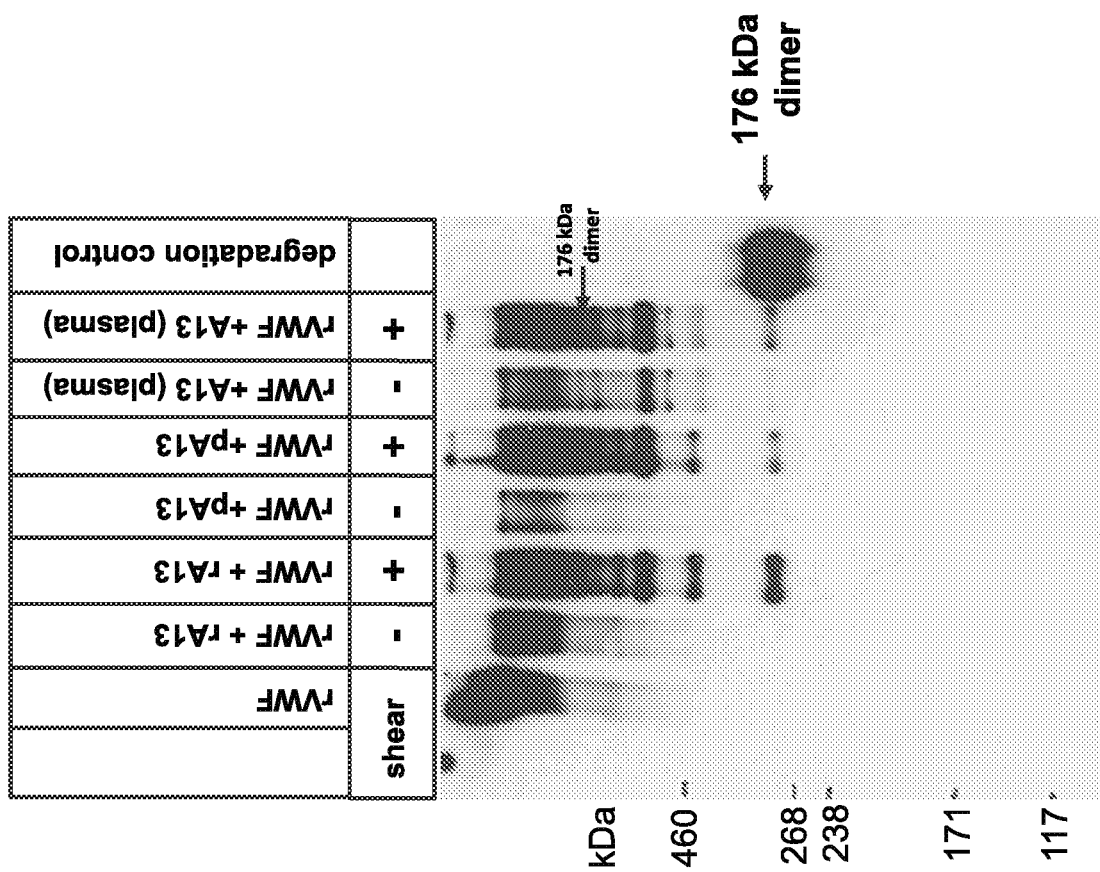
FIG. 17 shows the results of Western blot detection of the C-terminal VWF cleavage fragment after in vitro cleavage of 1 IU/mL rVWF by 0.2 U/mL of human recombinant ADAMTS13, human plasma-derived ADAMTS13, and normal human plasma in the presence and absence of shear stress.

The samples were applied to SDS-PAGE under non-reducing conditions on 3-8% Tris-Acetate gels (500 nL per lane) followed by Western blotting using an HRP-labeled rabbit anti-human VWF polyclonal antibody (Dako) in combination with an ECL plus technique. Results of this experiment are shown in FIG. 17. The degradation control marks the position of the 176 kDa dimer, which is specifically generated upon ADAMTS13 cleavage of VWF. Bands of the same mobility were discernible for the samples subjected to shear stress. By contrast, rVWF starting material and the otherwise identical samples kept under static conditions did not show the specific cleavage fragment.

The specificity of the observed VWF cleavage by ADAMTS13 was also analyzed by multimer analysis. rVWF (3 IU/mL final concentration) was mixed with rADAMTS13 (5 U/mL final concentration) in a reaction buffer containing 50 mM HEPES, 150 mM NaCl, 0.1 μM $ZnCl_2$, and 5 mM $CaCl_2$, pH=7.4. The reaction was started by subjecting the sample to a shear rate of 6000 $s^{-1}$ at 37° C. for 30 minutes and was stopped by the addition of EDTA (5 mM final concentration). As a negative control, an identical sample was similarly incubated in the absence of shear stress.

Figure 18A:
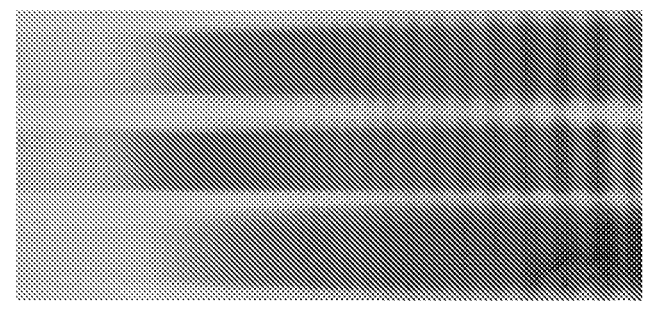
FIGS. 18A-18B show the changes in multimeric structure of rVWF at low (FIG. 18A) and high (FIG. 18B) resolution after in vitro cleavage by human ADAMTS13 in the presence and absence of shear stress.
Figure 18B:
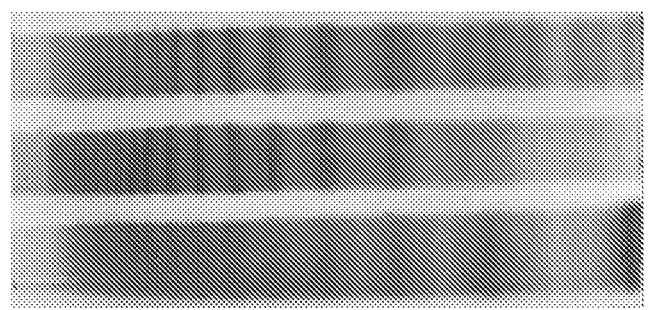

Low and high resolution multimer analysis (see FIGS. 18A and 18B) showed that rADAMTS13 induced degradation of rVWF and the formation of satellite bands, resulting in a pattern similar to that of normal human plasma (NHP, George King). No relevant changes in the multimer pattern were observed for the sample kept under static, yet otherwise identical, conditions.

The combined data demonstrate that ADAMTS13-dependent VWF cleavage, subject to in vitro conditions that more closely resemble the physiological one in blood circulation, is achieved and can be measured by the newly developed assay.

This assay is therefore also suitable for measuring ADAMTS13 activity in human plasma samples by the addition of rVWF as a substrate. Applicable are plasma samples with a wide range of ADAMTS13 activity levels.

Example 5

Detection Of The Effect Of Recombinant ADAMTS13 on Endogenous VWF in Plasma

The aim of this study is to further develop the method of detecting ADAMTS13 cleavage products in plasma in order to detect the effect of injected recombinant ADAMTS13 (rADAMTS13) on endogenous VWF in human and different animal samples. This will result in a method to choose the best suitable model for preclinical studies of rADAMTS13. Methods as set out herein above are used to test the effect of rADAMTS13 on the cleavage of rVWF and endogenous VWF in the plasma of various animal species, including human plasma.

The invention has been described in terms of particular embodiments found or proposed to comprise specific modes for the practice of the invention. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for testing effectiveness of a von Willebrand Factor (VWF) used in treating von Willebrand disease (VWD) in a subject comprising measuring VWF cleavage fragments in a blood sample from the subject before and after treatment, wherein an increase in VWF cleavage fragments after the treatment indicates that endogenous disintegrin and metalloproteinase with a thrombospondin type 1 motif, member 13 (ADAMTS13 ) in the subject is cleaving the VWF and wherein a decrease or absence of VWF cleavage fragments after the treatment indicates that endogenous ADAMTS13 in the subject is not cleaving the VWF; wherein a change in VWF cleavage fragment level is detected by measuring the level of one or more of a 140 kDa VWF fragment or a 176 kDa VWF fragment; and the measuring of VWF cleavage fragment level comprises performing Western blot analysis with a VWF antibody to visualize VWF cleavage fragments via enhanced chemiluminescence (ECL); wherein a change in VWF cleavage fragment level is detected by measuring the level of one or more of a 140 kDa VWF fragment or a 176 kDa VWF fragment; and the measuring of VWF cleavage fragment level comprises performing Western blot analysis with a VWF antibody to visualize VWF cleavage fragments via enhanced chemiluminescence (ECL).

2. The method of claim 1, wherein the Western blot analysis is carried out under non-reducing conditions.

3. The method of claim 1, wherein VWF fragments are visualized through use of a VWF antibody conjugated to a marker.

4. The method of claim 3, wherein the marker is alkaline phosphatase (ALP) or horseradish peroxidase (HRP).

5. The method of claim 1 wherein the VWF antibody is monoclonal or polyclonal.

6. The method of claim 1, wherein VWF cleavage fragments are detected at a sensitivity level of about 0.025 to about 0.05 Ag U/mL VWF.

7. The method of claim 1, wherein the blood sample is plasma or serum.

8. The method of claim 7, wherein the blood sample is plasma.

9. The method of claim 1, wherein the subject is a mammal.

10. The method of claim 9, wherein the mammalian subject is human, rabbit, monkey, dog, rat, mouse, or pig.

11. The method of claim 10, wherein the subject is human, rabbit, monkey, or dog.

12. The method of claim 11, wherein the subject is human.

13. The method of claim 1, wherein the VWF fragment is a 176 kDa VWF fragment.

14. The method of claim 1, wherein the VWF cleavage fragments are generated by the activity of the ADAMTS13 and carried out under shear stress.

15. The method of claim 14, wherein the shear stress comprises a shear rate of 100 to 10,000 s-1.

16. The method of claim 15, wherein the shear rate is 1,000 s-1 to 8,000 s-1.

17. The method of claim 15, wherein the shear rate is 6,000 s-1.

18. The method of claim 14, wherein the shear stress comprises a shear rate of 100 to 10,000 s-1 at a temperature of 20 ° C. to 40 ° C. for a period of time.

19. The method of claim 18, wherein the temperature is 30 ° C. to 40 ° C.

20. The method of claim 19, wherein the temperature is 37 ° C.

21. The method of claim 18, wherein the period of time ranges from 30 seconds to 1 hour.

22. The method of claim 21, wherein the time ranges from 15 minutes to 30 minutes.

23. The method of claim 22, wherein the time is 30 minutes or is 15 minutes.

* * * * *